US008796906B2

(12) United States Patent
Nishimura

(10) Patent No.: US 8,796,906 B2
(45) Date of Patent: Aug. 5, 2014

(54) PIEZOELECTRIC MOTOR, DRIVING DEVICE, ELECTRONIC COMPONENT CONVEYING DEVICE, ELECTRONIC COMPONENT INSPECTION DEVICE, PRINTING DEVICE, ROBOT HAND, AND ROBOT

(71) Applicant: Seiko Espon Corporation, Tokyo (JP)

(72) Inventor: Yoshiteru Nishimura, Shiojiri (JP)

(73) Assignee: Seiko Epson Corporation (JP)

(*) Notice: Subject to any disclaimer, the term of this patent is extended or adjusted under 35 U.S.C. 154(b) by 48 days.

(21) Appl. No.: 13/705,963

(22) Filed: Dec. 5, 2012

(65) Prior Publication Data

US 2013/0141717 A1 Jun. 6, 2013

(30) Foreign Application Priority Data

Dec. 6, 2011 (JP) ................................. 2011-266557
Dec. 6, 2011 (JP) ................................. 2011-266560

(51) Int. Cl.
*H02N 2/04* (2006.01)

(52) U.S. Cl.
USPC .................................................. 310/323.09

(58) Field of Classification Search
CPC ..... H02N 2/0095; H02N 2/103; H02N 2/026; H02N 2/028; H02N 20/04; H02N 2/043; H02N 2/02; H02N 2/0055; H01L 41/0906; H01L 41/0913
USPC ........................................ 310/323.01–323.21
See application file for complete search history.

(56) References Cited

U.S. PATENT DOCUMENTS

| | | |
|---|---|---|
| 5,180,941 A | 1/1993 | Seki et al. |
| 5,453,653 A | 9/1995 | Zumeris |
| 5,616,980 A | 4/1997 | Zumeris |
| 5,682,076 A | 10/1997 | Zumeris |
| 5,714,833 A | 2/1998 | Zumeris |
| 5,777,423 A | 7/1998 | Zumeris |
| 5,877,579 A | 3/1999 | Zumeris |
| 6,064,140 A | 5/2000 | Zumeris |
| 6,211,603 B1 | 4/2001 | Iino et al. |
| 6,455,983 B2 | 9/2002 | Dettmann et al. |
| 7,633,207 B2 | 12/2009 | Sakamoto |
| 7,663,292 B2 | 2/2010 | Adachi |
| 7,786,651 B2 | 8/2010 | Ue |
| 2005/0082950 A1* | 4/2005 | Zakoji ........................... 310/348 |
| 2010/0176689 A1* | 7/2010 | Elhayani et al. .............. 310/328 |
| 2011/0095650 A1* | 4/2011 | Sakano .................... 310/323.16 |

FOREIGN PATENT DOCUMENTS

| | | |
|---|---|---|
| JP | 03-155375 | 7/1991 |
| JP | 06-342121 | 12/1994 |
| JP | 11-346486 | 12/1999 |
| JP | 4035158 | 11/2007 |
| JP | 2008-187756 | 8/2008 |

(Continued)

*Primary Examiner* — Derek Rosenau

(74) *Attorney, Agent, or Firm* — Harness, Dickey & Pierce, P.L.C.

(57) ABSTRACT

A vibrating body is accommodated in a vibrating body case in a state where both sides of the vibrating body containing a piezoelectric material are sandwiched between buffer portions from a direction intersecting a bending direction of the vibrating body, and the buffer portions are pressed against the vibrating body using a pressing lid through elastic portions. Pressing plates are provided between the buffer portions and the elastic portions to restrict the movement of the pressing plates in a vibration direction of the vibrating body.

24 Claims, 13 Drawing Sheets

(56) References Cited

FOREIGN PATENT DOCUMENTS

| | | |
|---|---|---|
| JP | 2008-187757 | 8/2008 |
| JP | 2008-187768 | 8/2008 |
| JP | 2009-033788 | 2/2009 |
| JP | 4294061 | 4/2009 |
| JP | 4394158 | 10/2009 |
| JP | 2010-172079 | 8/2010 |

* cited by examiner

PIEZOELECTRIC MOTOR, DRIVING DEVICE, ELECTRONIC COMPONENT CONVEYING DEVICE, ELECTRONIC COMPONENT INSPECTION DEVICE, PRINTING DEVICE, ROBOT HAND, AND ROBOT

BACKGROUND

1. Technical Field

The present invention relates to a piezoelectric motor, a driving device, an electronic component conveying device, an electronic component inspection device, a printing device, a robot hand, and a robot.

2. Related Art

A piezoelectric motor which vibrates a member (vibrating body) formed of a piezoelectric material to drive an object is known. The piezoelectric motor can have a small size compared to an electromagnetic motor which rotates a rotor by an electromagnetic force, can obtain a large driving force, and can align the object with high precision. For this reason, the piezoelectric motor is used as an actuator for various devices, such as a driving mechanism of a camera.

The piezoelectric motor operates under the following principle. First, a vibrating body is formed to have a substantially rectangular parallelepiped shape, and has a convex portion protruding from an end surface in a longitudinal direction. If a voltage with a predetermined frequency is applied to the vibrating body, vibration in which the vibrating body is stretched and vibration in which the vibrating body is bent are simultaneously generated. When this happens, the end surface of the vibrating body starts an elliptical motion to rotate in one direction. Accordingly, if the convex portion provided at the end surface is pressed against the object, the object can be moved in a given direction with a frictional force acting between the convex portion and the object.

Under this operation principle, the piezoelectric motor is used in a state where the convex portion provided at the end surface of the vibrating body is pressed against the object. It is also necessary to retain the vibrating body such that the vibrating body does not escape or dislodge due to a reaction force received by the convex portion from the object when driving the object. Nevertheless, the vibration of the vibrating body should be permitted such that the convex portion performs an elliptical motion. Accordingly, a technique in which the vibrating body is housed in a retention case in a state where the convex portion protrudes, both sides of the vibrating body are supported from a bending direction by elastic members in the retention case, and the retention case is pressed against the object along with the vibrating body has been suggested.

JP-A-11-346486 is an example of the related art.

In recent years, however, there is an increasing demand for a reduction in the size and an improvement in the performance of a device having a piezoelectric motor mounted therein. Accordingly, in regard to the piezoelectric motor, there is demand for further reduction in size and improvement in driving precision.

There is a problem that it is difficult to efficiently use energy generated by the vibrating body so as to drive the object. This is because both sides of the vibrating body are supported from the bending direction, such that the vibration of the vibrating body is easily transmitted to the outside through the retention case, and the vibration transmitted to the outside cannot be used to drive the object.

SUMMARY

An advantage of some aspects of the invention is that it provides a technique capable of reducing the size of the piezoelectric motor and improving driving precision or a technique capable of efficiently driving an object.

An aspect of the invention is directed to a piezoelectric motor which vibrates a vibrating body containing a piezoelectric material, and brings a convex portion in an end surface of the vibrating body into contact with an object to move the object. The piezoelectric motor includes a vibrating body case which accommodates the vibrating body, a base which has a slide portion, on which the vibrating body case slides, and to which a vibrating body case is attached, a pressing elastic body which presses the convex portion protruding from the vibrating body case toward the object, and a side pressure elastic body which presses the vibrating body case toward the slide portion of the base from a direction intersecting a sliding direction of the vibrating body case, wherein an end surface of the side pressure elastic body in contact with the vibrating body case is fit into the vibrating body case.

According to the piezoelectric motor having this configuration, the vibrating body vibrates in a state where the convex portion of the vibrating body is in contact with the object along with the vibrating body case, thereby moving the object. Since the vibrating body case is pressed against the slide portion of the base by the side pressure elastic body, there is no case where the vibrating body escapes due to a reaction force received by the convex portion from the object when driving the object. The vibrating body case may slide in a direction close to or away from the object. Nevertheless, the side pressure elastic body which presses the vibrating body case against the slide portion from a direction intersecting the sliding direction of the vibrating body case is configured such that the end surface on the side in contact with the vibrating body case is fit into the vibrating body case.

With this, there is no case where the end surface of the side pressure elastic body relatively moves with respect to the vibrating body case. For this reason, since it is not necessary to provide an abrasion-resistant member or a roller between the end surface of the side pressure elastic body and the vibrating body case, the piezoelectric motor can be reduced in size. Of course, since the vibrating body case slides with respect to the object, in a structure in which the end surface of the side pressure elastic body is fit into the vibrating body case, the side pressure elastic body presses the vibrating body case against the slide portion of the base, and generates a force in a direction inhibiting the sliding of the vibrating body case. This force may act in a direction changing the force which presses the convex portion of the vibrating body against the object, and may change a frictional force generated between the convex portion and the object, as a result, changing the driving force of the piezoelectric motor. However, in practice, the effect of change in frictional force due to slipping of the end surface of the side pressure elastic body on the vibrating body case or change in frictional force when the roller provided between the side pressure elastic body and the vibrating body case rolls is large. Accordingly, with a structure in which the end surface of the side pressure elastic body does not slip on the vibrating body case, rather, change in the force which presses the convex portion of the vibrating body against the object can be reduced. If the end surface of the side pressure elastic body is fit into the vibrating body case, a change in the pressing force of the convex portion by the side pressure elastic body is merely a value smaller than variation in the pressing force due to manufacturing variation of the pressing elastic body. For the above reason, with the use of the structure in which the end surface of the side pressure elastic body is fit into the vibrating body case, it is possible to suppress a change in the force which presses the convex portion of the vibrating body against the object. As a result, the driving force of the piezoelectric motor becomes stable, thereby moving the object by the same distance each time the convex portion performs an elliptical motion with the vibration of the vibrating body. In this way, according to the piezoelectric motor of the aspect of the invention, it becomes possible to reduce the size of the piezoelectric motor and to improve driving precision.

It is sufficient that the pressing elastic body or the side pressure elastic body can press the vibrating body case, and various types of springs, such as a coil spring or a flat spring, may be used. When a flat spring is used as the side pressure elastic body, a portion in the surface of the side pressure elastic body which is in contact with the vibrating body case and exerts a force becomes the end surface of the side pressure elastic body. If the coil spring is used in a highly deformed state, even when the vibrating body case slides, the coil spring can be used in a state where the pressing force is hardly changed. For this reason, the coil spring can be preferably used as the pressing elastic body or the side pressure elastic body. It should suffice that the end surface of the side pressure elastic body is accommodated so as not to slip on the vibrating body case when the vibrating body case slides. Accordingly, as the form in which the end surface of the side pressure elastic body is fit into the vibrating body case, for example, a concave portion may be provided in the vibrating body case and the end surface of the pressure elastic body may be fit into the concave portion, or a protrusion may be provided from the vibrating body case, and the end surface of the side pressure elastic body may be fit into the protrusion. A protrusion may be provided from the end surface of the side pressure elastic body, and the protrusion may be fit into a concave portion provided in the vibrating body case.

In the above-described piezoelectric motor, the end surface of the side pressure elastic body on a side not in contact with the vibrating body case may be supported by a side pressure elastic body retention portion, such that the end surface of the side pressure elastic body on a side in contact with the side pressure elastic body retention portion may be fit into the side pressure elastic body retention portion.

With this, there is no case where the end surface of the side pressure elastic body on the side not in contact with the vibrating body case slips. For this reason, it is possible to avoid a change in the frictional force due to slipping, and change in the force which presses the convex portion of the vibrating body against the object. As a result, it becomes possible to further improve driving precision of the piezoelectric motor.

In the above-described piezoelectric motor, instead of providing the pressing elastic body on the rear side of the vibrating body case (the opposite side to the side facing the object), the pressing elastic body may be provided on a side on which the slide portion is provided with respect to the vibrating body case or a side on which the side pressure elastic body is provided with respect to the vibrating body case.

With this, the length of the piezoelectric motor can be shortened compared to a case where the pressing elastic body is provided on the rear side of the vibrating body case. As a result, it becomes possible to further reduce the size of the piezoelectric motor.

A driving device, a printing device, a robot hand, a robot, or the like may be constituted by the above-described piezoelectric motor.

With the above-described piezoelectric motor, it is possible to realize a reduction in the size with high driving precision. Therefore, if the driving device, the printing device, the robot hand, the robot, or the like is constituted by the above-described piezoelectric motor, it is possible to obtain a driving device, a printing device, a robot hand, a robot, or the like which is of small size and has high performance.

An electronic component inspection device described below may be constituted by the above-described piezoelectric motor. That is, an electronic component inspection device which mounts a held electronic component in an inspection socket, and inspects the electrical characteristics of the electronic component may be configured to align the electronic component with respect to the inspection socket by the above-described piezoelectric motor.

An electronic component conveying device described below may be constituted by the above-described piezoelectric motor. That is, an electronic component conveying device which conveys a held electronic component may be configured to align the electronic component by the above-described piezoelectric motor.

With the above-described piezoelectric motor, it is possible to realize a reduction in the size with high driving precision, thereby aligning the electronic component with high precision and realizing a small electronic component conveying device.

The electronic component conveying device may be implemented as the following form. That is, an electronic component conveying device may be configured to include a holding device which holds an electronic component, a moving device which moves the holding device in the directions of three axes in total of a first axis and a second axis perpendicular to each other and a third axis perpendicular to the first axis and the second axis, a control device which controls the operation of the moving device, wherein the holding device is embedded with a first piezoelectric motor which moves the electronic component in the direction of the first axis, a second piezoelectric motor which moves the electronic component in the direction of the second axis, and a third piezoelectric motor which rotates the electronic component around the third axis, and the first to third piezoelectric motors are the above-described piezoelectric motor.

The electronic component inspection device may be implemented as the following form.

That is, an electronic component inspection device which mounts an electronic component in an inspection socket, and inspects the electrical characteristics of the electronic component may be configured to include a holding device which holds the electronic component, a moving device which moves the holding device in the directions of three axes in total of a first axis and a second axis perpendicular to each other and a third axis perpendicular to the first axis and the second axis, an imaging device which is provided on the first axis or the second axis when viewed from the inspection socket to detect the posture of the electronic component mounted in the inspection socket, an upstream-side stage which conveys the electronic component from the inspection socket to a predetermined position on the first axis or the second axis connecting the imaging device, a downstream-side stage which conveys the electronic component from a predetermined position opposite to the side on which the imaging device is provided when viewed from the inspection socket, and a control device which controls the operation of the moving device, wherein the control device includes a first control unit which moves the holding device holding the electronic component conveyed by the upstream-side stage onto the imaging device, a second control unit which moves the holding device to mount the electronic component whose posture is confirmed by the imaging device in the inspection socket, and a third control unit which moves the holding device to place the electronic component whose electrical characteristics are inspected in the inspection socket from the inspection socket to the downstream-side stage, the holding device is embedded with a first piezoelectric motor which moves the electronic component in the direction of the first axis on the basis of the posture of the electronic component detected by the imaging device, a second piezoelectric motor which moves the electronic component in the direction of the second axis on the basis of the posture of the electronic component detected by the imaging device, and a third piezoelectric motor which rotates the electronic component around the third axis on the basis of the posture of the electronic component detected by the imaging device, and the first to third piezoelectric motors are the above-described piezoelectric motor.

The electronic component inspection device having this configuration can mount the electronic component in the inspection socket after the posture of the electronic component is adjusted by the first to third piezoelectric motors provided in the holding device. Since the above-described piezoelectric motor can be of small size and can drive the object with high precision, the piezoelectric motor is particularly excellent as the first to third piezoelectric motors provided in the holding device.

The electronic component inspection device according to the aspect of the invention may have the following configuration.

That is, an electronic component inspection device which mounts a held electronic component in an inspection socket, and inspects the electrical characteristics of the electronic component may be configured to include a piezoelectric motor which aligns the electronic component with respect to the inspection socket, the piezoelectric motor includes a vibrating body which is formed to contain a piezoelectric material, and has a convex portion protruding in an end surface, a vibrating body case which accommodates the vibrating body, a base which has a slide portion, on which the vibrating body case slides, and to which a vibrating body case is attached, a pressing elastic body which presses the convex portion protruding from the vibrating body case toward the object, and a side pressure elastic body which presses the vibrating body case toward the slide portion of the base from a direction intersecting a sliding direction of the vibrating body case, wherein an end surface of the side pressure elastic body on a side in contact with the vibrating body case is fit into the vibrating body case.

The electronic component conveying device according to the aspect of the invention may have the following configuration.

That is, an electronic component conveying device which conveys a held electronic component may be configured to include a piezoelectric motor which aligns the electronic component, the piezoelectric motor includes a vibrating body which is formed to contain a piezoelectric material, and has a convex portion protruding in an end surface, a vibrating body case which accommodates the vibrating body, a base which has a slide portion, on which the vibrating body case slides, and to which a vibrating body case is attached, a pressing elastic body which presses the convex portion protruding from the vibrating body case toward the object, and a side pressure elastic body which presses the vibrating body case toward the slide portion of the base from a direction intersecting a sliding direction of the vibrating body case, wherein an end surface of the side pressure elastic body on a side in contact with the vibrating body case is fit into the vibrating body case.

Another aspect of the invention is directed to a piezoelectric motor in which stretching vibration and bending vibration are generated in a vibrating body to move an object. The piezoelectric motor includes a vibrating body which is formed to contain a piezoelectric material, and has a convex portion protruding in an end surface, a vibrating body case which accommodates the vibrating body, a pressing elastic body which presses the vibrating body case in a direction bringing the convex portion of the vibrating body into contact with an object, buffer portions which sandwich both sides of the vibrating body from a direction intersecting a bending direction of the vibrating body in the vibrating body case, and are formed to contain a material having dynamic viscoelasticity, pressing lids which are attached to the vibrating body case, disk springs which are provided between the pressing lids and the buffer portions, and are compressed by the pressing lids, and pressing plates which are provided between the buffer portions and the disk springs to restrict the movement in stretching direction and a bending direction of the vibrating body.

In the piezoelectric motor of the aspect of the invention having this configuration, since both surfaces of the vibrating body accommodated in the vibrating body case are sandwiched by the buffer portions from the direction intersecting the bending direction of the vibrating body, the vibration of the vibrating body is not easily transmitted to the vibrating body case, thereby efficiently driving the object. Since the buffer portions are formed to contain a material having dynamic viscoelasticity, the vibration of the vibrating body is attenuated when the buffer portions are deformed. From this meaning, the vibration of the vibrating body is not easily transmitted to the vibrating body case. The dynamic viscoelasticity (tan $\delta$) is the following index. If sinusoidal distortion $\epsilon$ is given to a material in a tensile mode, while sinusoidal stress $\sigma$ occurs in the material, the phase of stress $\sigma$ is delayed by a phase $\delta$ with respect to the input distortion. An index which is obtained by quantifying dynamic viscosity of the material by the phase $\delta$ is the dynamic viscoelasticity (tan $\delta$). That is, the condition that the dynamic viscoelasticity is large, that is, the phase $\delta$ is large refers to a transmission delay of the given distortion inside the material. In other words, the transmission of the vibration is delayed, thereby suppressing the transmission of the vibration to the vibrating body case. The buffer portions are pressed against the vibrating body by the disk springs compressed by the pressing lids. For this reason, even when the dimension of the vibrating body or the buffer portions varies in the sandwiching direction of the vibrating body (the direction intersecting the bending direction of the vibrating body), variation can be absorbed by elastic deformation of the disk springs. The pressing plates are provided between the buffer portions and the disk springs, and the pressing plates are configured such that the movement in the vibration direction of the vibrating body (the stretching direction and the bending direction of the vibrating body) is restricted. The term "the movement is restricted" means that movement is not possible if the movement exceeds a certain amount of movement. For this reason, even when the convex portion of the vibrating body receives a reaction force from the object, since the movement of the pressing plate is restricted, there is no case where the disk springs are significantly deformed in a shearing direction. In this way, according to the aspect of the invention, variation in dimension in the sandwiching direction of the vibrating body or the buffer portions is absorbed by elastic deformation of the disk springs, and nevertheless, the disk springs can be hardly deformed in the vibration direction of the vibrating body or in the direction in which the reaction force from the object is received. As a result, a complicated operation to actually measure the thickness of the vibrating body or the buffer portions, to select and assemble the buffer portions for the vibrating body, or the like, is not required, making it possible to easily manufacture a piezoelectric motor.

In the piezoelectric motor, the pressing plates may be fit into the pressing lids, such that the movement of the pressing plate is restricted. For example, a concave portion may be formed in a portion of each pressing lid, a portion of the pressing plate (the end surface of the pressing plate, the convex portion protruding from the pressing plate, or the like) may be fit into the concave portion of the pressing lid, and as a result, the pressing plates cannot move in the vibration direction (the stretching direction and the bending direction) of the vibrating body. Of course, the entire pressing plate may be fit into the concave portion of the pressing lid. When a concave portion is formed in the pressing plate, the convex portion protruding from the pressing lid may be fit into the concave portion of the pressing plate.

With this, it becomes possible to simply realize a structure in which the buffer portions are pressed against the vibrating body by the disk springs, and the movement of the pressing plates is restricted.

In the above-described piezoelectric motor, unevenness may be formed in the surfaces (contact surfaces) of the portions of the pressing plates in contact with the buffer portions. On the contrary, unevenness may be formed in the surfaces (contact surfaces) of the portions of the buffer portions in contact with the pressing plates.

With this, since unevenness formed in the pressing plates bite into the buffer portions or unevenness formed in the buffer portions bite into the pressing plate with the force when the disk spring presses the pressing plates, the buffer portions hardly slip on the contact surfaces with the pressing plates. For this reason, there are few cases where the vibrating body moves with the reaction force received by the convex portion during the driving of the object along with the buffer portions. The unevenness formed in the pressing plates or the buffer portions may be various types of unevenness. For example, saw-toothed unevenness in which the tip of the convex portion is sharp may be used, or fine unevenness in which the surface is grained may be used. Alternatively, unevenness may be formed on both sides of the pressing plates and the buffer portions, and the unevenness formed on one side may be fit into the unevenness formed on the other side.

The piezoelectric motor according to the aspect of the invention may have the following configuration.

That is, a piezoelectric motor in which stretching vibration and bending vibration are generated in a vibrating body to move an object may be configured to include a vibrating body which is formed to contain a piezoelectric material, and has a convex portion protruding in an end surface, a vibrating body case which accommodates the vibrating body, a pressing elastic body which presses the vibrating body case in a direction bringing the convex portion of the vibrating body into contact with an object, buffer portions which sandwich both sides of the vibrating body from a direction intersecting a bending direction of the vibrating body in the vibrating body case, and are formed to contain a material having dynamic viscoelasticity, pressing lids which are attached to the vibrating body case, disk springs which are compressed by the pressing lids, and pressing plates which are provided between the disk springs and the buffer portions.

In the piezoelectric motor of the aspect of the invention having this configuration, since both sides of the vibrating body accommodated in the vibrating body case are sandwiched by the buffer portions from the direction intersecting the bending direction of the vibrating body, the vibration of the vibrating body is not easily transmitted to the vibrating body case, thereby efficiently driving the object. Since the buffer portions are formed to contain a material having dynamic viscoelasticity, the vibration of the vibrating body is attenuated when the buffer portions are deformed. From this meaning, the vibration of the vibrating body is not easily transmitted to the vibrating body case. The dynamic viscoelasticity (tan δ) is the following index. If sinusoidal distortion ε is given to a material in a tensile mode, while sinusoidal stress σ occurs in the material, the phase of stress σ is delayed by a phase δ with respect to the input distortion. An index which is obtained by quantifying dynamic viscosity of the material by the phase δ is the dynamic viscoelasticity (tan δ). That is, the condition that the dynamic viscoelasticity is large, that is, the phase δ is large refers to a transmission delay of the given distortion inside the material. In other words, the transmission of the vibration is delayed, thereby suppressing the transmission of the vibration to the vibrating body case. The buffer portions are pressed against the vibrating body by the disk springs compressed by the pressing lids. For this reason, even when the dimension of the vibrating body or the buffer portions varies in the sandwiching direction of the vibrating body (the direction intersecting the bending direction of the vibrating body), variation in dimension can be absorbed by elastic deformation of the disk springs. The disk springs have a shape which is not easily deformed in the vibration direction (the stretching direction and the bending direction) of the vibrating body. The disk springs are pressed by the pressing lids, and the corners of the disk spring bit into the pressing plates and the pressing lids. For this reason, there is no case where the disk springs slip with respect to the pressing plates or the pressing lids. Accordingly, the pressing plates to the pressing lids can be substantially handled as a rigid body in the vibration direction of the vibrating body (the stretching direction and the bending direction of the vibrating body) and the direction in which the reaction force from the object is received. For this reason, according to the aspect of the invention, variation in dimension in the sandwiching direction of the vibrating body or the buffer portions is absorbed by deformation of the disk springs, and nevertheless, there is no effect of the disk springs in the vibration direction of the vibrating body or in the direction in which the reaction force from the object is received. As a result, a complicated operation to actually measure the thickness of the vibrating body or the buffer portions, to select and assemble the buffer portions for the vibrating body, or the like, is not required, making it possible to easily manufacture a piezoelectric motor. With this, there is no adverse effect on the performance of the piezoelectric motor.

In the above-described piezoelectric motor, a groove (first groove) into which a corner portion of each disk spring is fit may be formed in advance in a portion of the corresponding pressing plate with which the corner portion of the disk spring is in contact, and a groove (second groove) into which the corner portion of the disk spring may be formed in advance in a portion of the corresponding pressing lid with which the corner portion of the disk spring is in contact.

With this, as the material for the pressing plates or the pressing lids, a solid material compared to the disk springs (a material whose surface is subjected to thermal treatment) or the like may be used. If the first groove or the second groove is deeply formed, since the disk springs can be reliably retained with respect to the pressing plates or the pressing lids, it is possible to reliably prevent the disk springs from slipping with respect to the pressing plates or the pressing lids.

In the above-described piezoelectric motor, a concave portion into which an outer circumferential portion of each disk spring may be fit may be formed in either the corresponding pressing plate or the corresponding pressing lid.

With this, when superimposing and assembling the pressing plate, the disk spring, and the pressing lid, since the disk spring can be fit into the concave portion, the assembling operation is facilitated. From the viewpoint of ease of the assembling operation, it should suffice that the outer circumferential portion of the disk spring is loosely fit into the concave portion such that the disk spring does not move significantly. However, if the outer circumferential portion of the disk spring is fit into the concave portion in a state where the disk spring does not move, the assembling operation is facilitated, and it also becomes possible to reliably prevent the disk spring from moving with respect to the pressing plate or the pressing lid during the operation of the piezoelectric motor. The shape of the concave portion in top view (the shape when viewed from the pressing direction by the pressing lid) is preferably formed such that the outer circumferential portion of the disk spring is fit therein. Accordingly, while the same circular shape as the disk spring may be used, for example, a polygonal shape or the like may be used.

In the above-described piezoelectric motor, a convex portion into which an inner circumferential portion of each disk spring is fit may be formed in either the corresponding pressing plate or the corresponding pressing lid.

With this, when superimposing and assembling the pressing plate, the disk spring, and the pressing lid, since the disk spring can be fit into the convex portion, the assembling operation is facilitated. From the viewpoint of ease of the assembling operation, it should suffice that the inner circumferential portion of the disk spring is loosely fit into the convex portion such that the disk spring does not move significantly. However, if the inner circumferential portion of the disk spring is fit into the convex portion in a state where the disk spring does not move, the assembling operation is facilitated, and it also becomes possible to reliably prevent the disk spring from moving with respect to the pressing plate or the pressing lid during the operation of the piezoelectric motor. The shape of the convex portion in top view (the shape when viewed from the pressing direction by the pressing lid) is preferably formed such that the inner circumferential portion of the disk spring is fit therein. Accordingly, while the same circular shape as the disk spring may be used, for example, a polygonal shape or the like may be used.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiment 1

Hereinafter, the configuration of a piezoelectric motor according to Embodiment 1 will be described.

Device Configuration

Figure 1A:
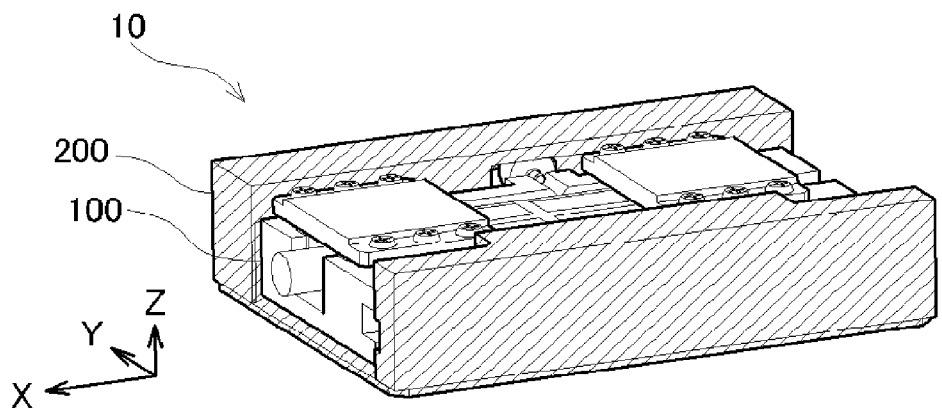
FIGS. 1A and 1B are explanatory views showing the basic configuration of a piezoelectric motor of Embodiment 1.
Figure 1B:
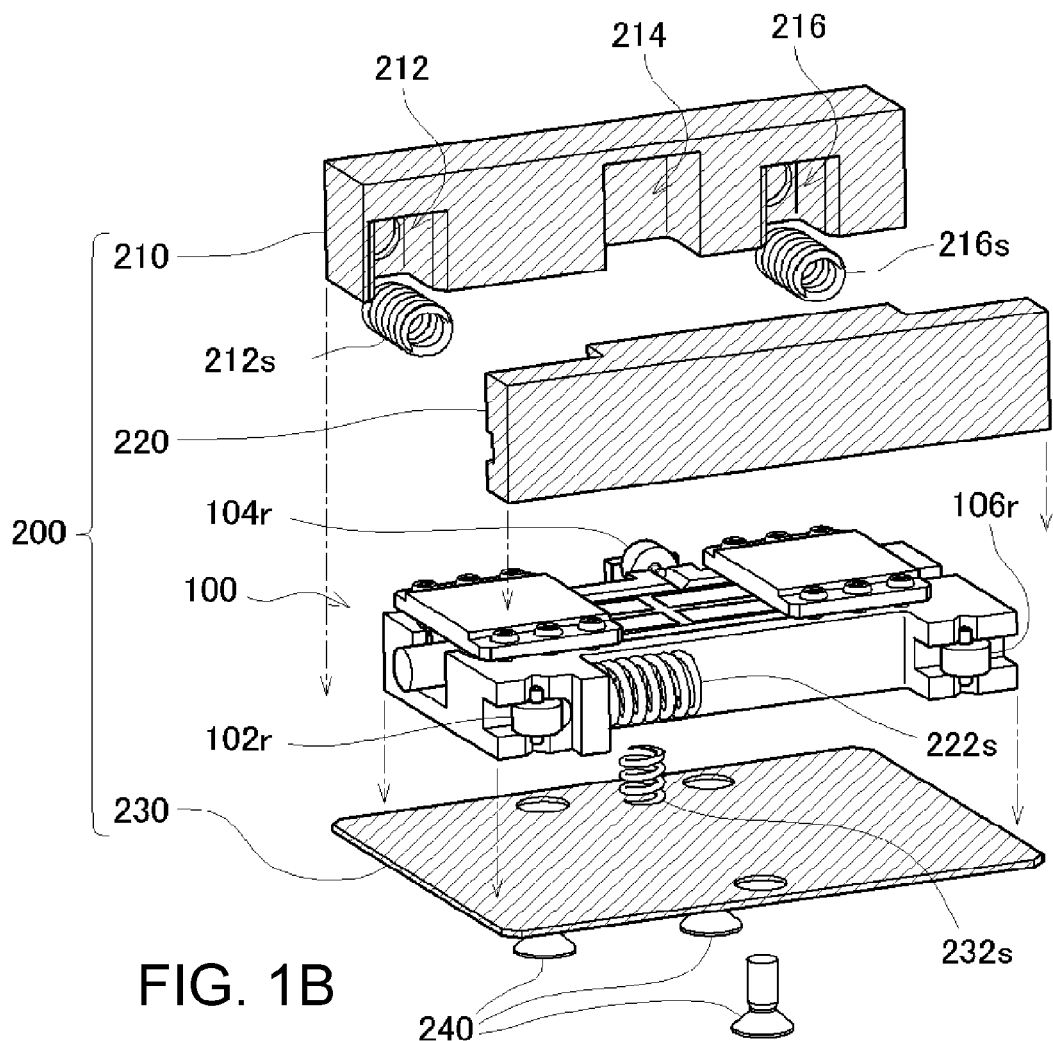

FIGS. 1A and 1B are explanatory views showing the basic configuration of a piezoelectric motor 10 of this embodiment. FIG. 1A is an overall view of the piezoelectric motor 10 of this embodiment, and FIG. 1B is an exploded view. As shown in FIG. 1A, the piezoelectric motor 10 of this embodiment has a main portion 100 and a base portion 200. The main portion 100 is fit into the base portion 200, and is slidable in one direction in this state. In this specification, the sliding direction of the main portion 100 is referred to as an X direction. As shown in the drawing, the directions perpendicular to the X direction are respectively referred to as a Y direction and a Z direction.

The main portion 100 and the base portion 200 respectively have a plurality of components. For example, the base portion 200 is configured such that a first sidewall block 210 and a second sidewall block 220 are fastened to both sides of an upper surface of a substrate 230 substantially having a rectangular shape by locking screws 240 (see FIG. 1B). When assembling the piezoelectric motor 10, the first sidewall block 210 and the second sidewall block 220 are attached to the substrate 230 by the locking screws 240 from above the main portion 100.

The first sidewall block 210 has three concave portions of a front housing 212, a central housing 214, and a rear housing 216. When attaching the first sidewall block 210 to the substrate 230, attachment is made in a state where a front-side pressure spring 212s is accommodated in the front housing 212, and a rear-side pressure spring 216s is accommodated in the rear housing 216. As a result, the main portion 100 is in a state of being pressed to the second sidewall block 220 by the front-side pressure spring 212s and the rear-side pressure spring 216s. A front roller 102r and a rear roller 106r are attached onto the lateral surface side of the main portion 100 facing the second sidewall block 220. A pressure spring 222s is provided on the lateral surface side of the main portion 100. The pressure spring 222s presses the main portion 100 at a location on the rear side of the front roller 102r in the X direction. In this embodiment, the front-side pressure spring 212s and the rear-side pressure spring 216s correspond "side pressure elastic body" and "second biasing member" according to the invention, and the pressure spring 222s corresponds to the "pressing elastic body" and "first biasing member" according to the invention. The base portion 200 corresponds to the "base" according to the invention, and the first sidewall block 210 and the second sidewall block 220 constituting the base portion 200 respectively correspond to the "side pressure elastic body retention portion" and the "slide portion" according to the invention.

A pressing roller 104r in the Z direction (upwards in the drawing) is provided on the lateral surface of the main portion 100 opposite to the side on which the front roller 102r and the rear roller 106r are provided. When the first sidewall block 210 is attached, the pressing roller 104r is accommodated in the central housing 214 of the first sidewall block 210. A pressing spring 232s is provided between the rear side of a portion where the pressing roller 104r of the main portion 100 is provided and the substrate 230. For this reason, the pressing roller 104r is in a state of being pressed in the Z direction (upward in the drawing) with respect to the inner surface of the central housing 214.

Figure 2:
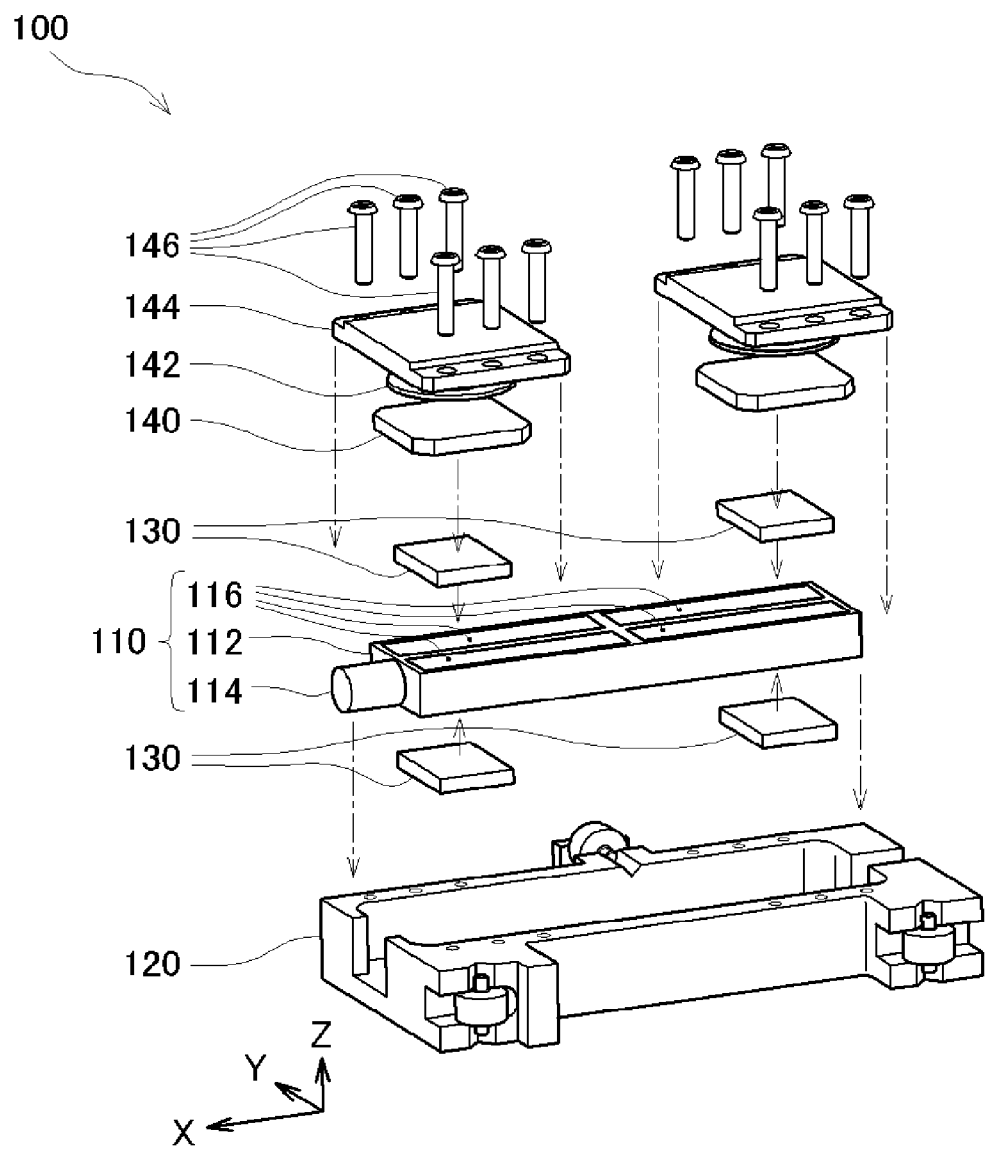
FIG. 2 is an exploded view showing the structure of a main portion.

FIG. 2 is an exploded view showing the structure of the main portion 100. The main portion 100 has a structure in which a vibration unit 110 is accommodated in a vibrating body case 120. The vibration unit 110 has a vibrating body 112 which is formed of a piezoelectric material to have a substantially rectangular parallelepiped shape, a ceramic driving convex portion 114 (a cylindrical protrusion) which is attached to an end surface in a longitudinal direction (X direction) of the vibrating body 112, four front electrodes 116 which are provided by quartering one lateral surface of the vibrating body 112, and the like. Though not shown in FIG. 2, in the lateral surface opposite to the side on which the four front electrodes 116 are provided, a rear electrode which substantially covers the entire lateral surface is provided. The rear electrode is grounded. In this embodiment, the driving convex portion 114 corresponds to the "convex portion" according to the invention.

The vibration unit 110 is accommodated in the vibrating body case 120 in a state where both lateral surfaces (in FIG. 2, both lateral surfaces in the Z direction) in which the front electrodes 116 and the rear electrode are provided are sandwiched by buffer portions 130. Pressing plates 140, disk springs 142, and pressing lids 144 are placed from above the buffer portions 130 on the front electrode 116 side, and the pressing lids 144 are fastened to the vibrating body case 120 by locking screws 146. The buffer portions 130 are formed of a material (polyimide resin, rubber, elastomer, or the like) having dynamic viscoelasticity. For this reason, while the vibration unit 110 is pressed by the spring force of the disk springs 142, the buffer portions 130 are shear-deformed, such that the vibrating body 112 is accommodated in the vibrating body case 120 in a vibratable state.

Operation Principle of Piezoelectric Motor

FIGS. 3A to 3D are explanatory views showing the operation principle of the piezoelectric motor 10. The piezoelectric motor 10 operates by the elliptical motion of the driving convex portion 114 of the vibration unit 110 when a voltage is applied to the front electrodes 116 of the vibration unit 110 in a given period. The elliptical motion of the driving convex portion 114 of the vibration unit 110 is for the following reason.

Figure 3A:
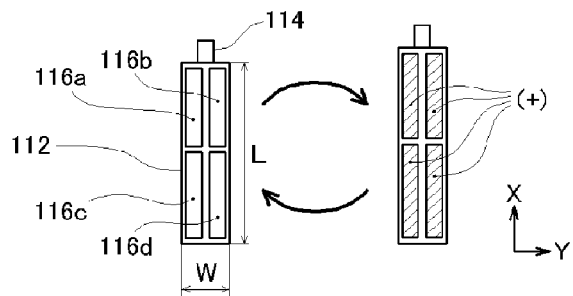
FIGS. 3A to 3D are explanatory views showing an operation principle of a piezoelectric motor.

First, as well known in the art, the vibrating body 112 expands if a positive voltage is applied. Accordingly, as shown in FIG. 3A, if a positive voltage is applied to all of the four front electrodes 116, and the applied voltage is then released repeatedly, the vibrating body 112 repeatedly expands and contracts in the longitudinal direction (X direction). In this way, an operation in which the vibrating body 112 repeatedly expands and contracts in the longitudinal direction (X direction) is referred to as "stretching vibration". If the frequency at which the positive voltage is applied is changed, the amount of expansion and contraction rapidly increases when a specific frequency is reached, and a type of resonance phenomenon occurs. The frequency (resonance frequency) at which resonance occurs due to stretching vibration is determined by the physical property of the vibrating body 112 and the dimension (width W, length L, thickness T) of the vibrating body 112.

Figure 3B:
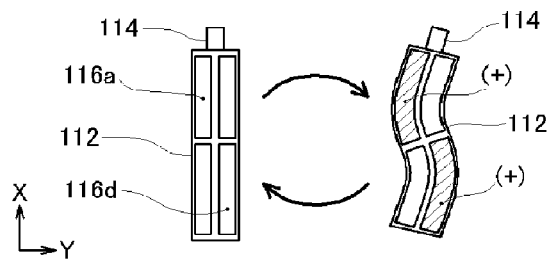
Figure 3C:
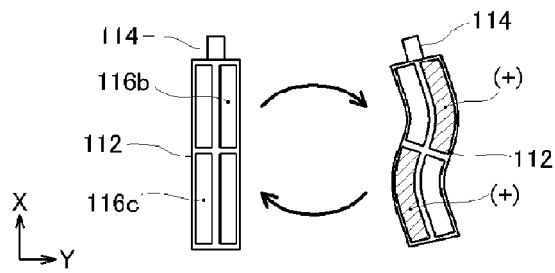

As shown in FIG. 3B, the positive voltage is alternately applied to sets of diagonally opposite two front electrodes 116 (a set of front electrode 116a and front electrode 116d and a set of front electrode 116b and front electrode 116c). When this happens, the vibrating body 112 repeats an operation such that the tip portion in the longitudinal direction (X direction) (a portion to which the driving convex portion 114 is attached) shakes the head thereof in a right direction or a left direction in the drawing. For example, as shown in FIG. 3B, if the positive voltage is applied to the set of front electrode 116a and front electrode 116d in a given period, the vibrating body 112 repeats an operation such that the tip portion (driving convex portion 114) shakes in the right direction on the drawing. As shown in FIG. 3C, if the positive voltage is applied to the set of front electrode 116b and front electrode 116c in a given period, the vibrating body 112 repeats an operation such that the tip portion shakes in the left direction on the drawing. This operation of the vibrating body 112 is referred to as "bending vibration". In regard to the bending vibration, there is the resonance frequency which is determined by the physical property of the vibrating body 112 and the dimension (width W, length L, thickness T) of the vibrating body 112. Accordingly, if the positive voltage is alternately applied to the sets of diagonally opposite two front electrodes 116 at the resonance frequency, the vibrating body 112 largely shakes the head thereof in the right direction or the left direction.

Figure 3D:
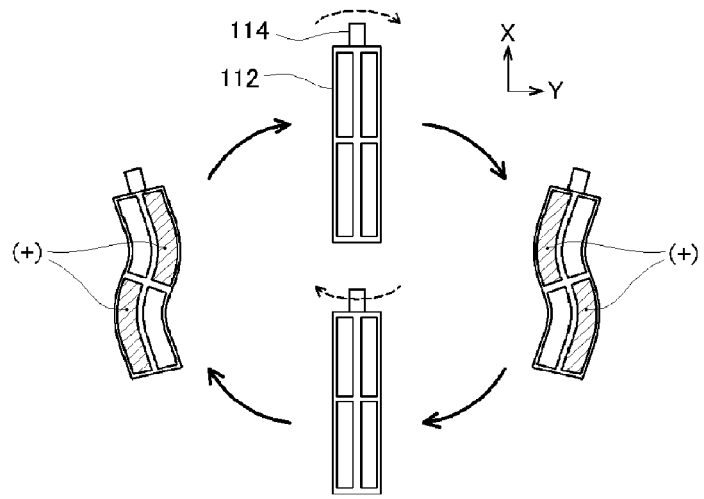

The resonance frequency of the stretching vibration shown in FIG. 3A and the resonance frequency of the bending vibration shown in FIG. 3B or 3C are determined by the physical property of the vibrating body 112 or the dimension (width W, length L, thickness T) of the vibrating body 112. Accordingly, if the dimension (width W, length L, thickness T) of the vibrating body 112 is appropriately selected, the two resonance frequencies can coincide with each other. If the voltage in the form of the bending vibration shown in FIG. 3B or 3C is applied to the vibrating body 112 at the resonance frequency, the bending vibration shown in FIG. 3B or 3C occurs, and the stretching vibration of the FIG. 3A is induced by resonance. As a result, when a voltage is applied in the form shown in FIG. 3B, the tip portion (the portion to which the driving convex portion 114 is attached) of the vibrating body 112 starts an elliptical motion in a clockwise direction on the drawing. When a voltage is applied in the form shown in FIG. 3C, the tip portion of the vibrating body 112 starts an elliptical motion in a counterclockwise direction on the drawing. FIG. 3D is a transition diagram showing a change form in a rotation direction of an elliptical motion when an applied voltage (driving method) is changed.

The piezoelectric motor 10 drives an object by the elliptical motion. That is, the elliptical motion is generated in a state where the driving convex portion 114 of the vibrating body 112 is pressed against the object. In this case, the driving convex portion 114 repeats an operation to move from left to right (or from right to left) in a state of being pressed against the object when the vibrating body 112 expands, and to return the original position in a state of being away from the object when the vibrating body 112 contracts. As a result, the object is driven in one direction by a frictional force applied from the driving convex portion 114. Since the frictional force applied to the object is equal to a driving force which is generated between the object and the driving convex portion 114, the magnitude of the driving force is determined by a frictional coefficient between the driving convex portion 114 and the object and a force when the driving convex portion 114 is pressed against the object.

As will be apparent from the operation principle of the piezoelectric motor 10 described above, it is necessary that the piezoelectric motor 10 is used in a state where the driving convex portion 114 is pressed against the object. For this reason, in the piezoelectric motor 10, the main portion 100 including the driving convex portion 114 is slidable with respect to the base portion 200, and the driving convex portion 114 protruding from the main portion 100 is pressed against the object by the pressure spring 222s provided between the main portion 100 and the base portion 200 (see FIGS. 1A and 1B).

If the object is driven, the driving convex portion 114 receives a reaction force from the object. The reaction force is transmitted to the main portion 100. As described above, while the main portion 100 should be slidable with respect to the base portion 200, if the main portion 100 escapes in a direction perpendicular to the sliding direction due to the reaction force received during driving or otherwise, a sufficient driving force cannot be transmitted to the object. If the main portion 100 escapes, the amount of movement of the driving convex portion 114 decreases, such that the amount of driving of the object becomes small. Since the amount of misalignment/escape of the main portion 100 may not be constantly stable, the amount of driving of the object becomes unstable. Accordingly, as shown in FIGS. 1A and 1B, in the piezoelectric motor 10, the main portion 100 is pressed against the second sidewall block 220 from the direction perpendicular to the sliding direction of the main portion 100 by the front-side pressure spring 212s and the rear-side pressure spring 216s. In the piezoelectric motor 10, the front-side pressure spring 212s and the rear-side pressure spring 216s are attached in the following manner.

The piezoelectric motor 10 uses the vibrating body 112 to vibrate in the stretching direction (X direction) and the bending direction (Y direction) in a state where the driving convex portion 114 is pressed against the object. For this reason, in the vibrating body case 120, it is necessary that the vibrating body 112 is stored in a state where the vibration in the stretching direction and the bending direction is permitted.

When the vibrating body 112 vibrates to move the object, the reaction force from the object is applied to the driving convex portion 114. If the vibrating body 112 moves in the vibrating body case 120 due to the reaction force, a sufficient driving force may not be applied to the object, and the amount of movement of the driving convex portion 114 decreases, such that the amount of driving of the object becomes small. Since the amount of escape of the main portion 100 may not be constantly stable, the amount of driving of the object becomes unstable. Accordingly, in the piezoelectric motor 10, as shown in FIG. 2, a structure in which both lateral surfaces of the vibrating body 112 are sandwiched by the buffer portions 130 from the direction (Z direction) intersecting the bending direction of the vibrating body 112 in the vibrating body case 120 to retain the vibrating body 112 is used. In this retention structure, the buffer portions 130 are deformed in a shearing direction to permit the vibration of the vibrating body 112, and with rigidity when the buffer portions 130 are deformed in the shearing direction, the vibrating body 112 can be retained so as not to move due to the reaction force from the object.

In this retention structure, since both sides of the vibrating body 112 which is formed of a piezoelectric material and liable to undergo manufacturing variation are sandwiched by the buffer portions 130 which are formed of polyimide resin or the like and liable to undergo manufacturing variation. For this reason, since manufacturing variation of the vibrating body 112 and the buffer portions 130 is accumulated, large variation is liable to occur in the dimension in the thickness direction (Z direction). Since the buffer portions 130 should have rigidity such that the vibrating body 112 does not move even when the reaction force from the object is received, variation in dimension is not easily absorbed by the buffer portion 130. Accordingly, in the piezoelectric motor 10, a structure in which the vibrating body 112 is sandwiched by the buffer portions 130, and the buffer portions 130 are pressed against the vibrating body 112 by the pressing plates 140, the disk springs 142, and the pressing lids 144 to sandwich the vibrating body 112 is used.

Embodiment 2

Figure 4A:
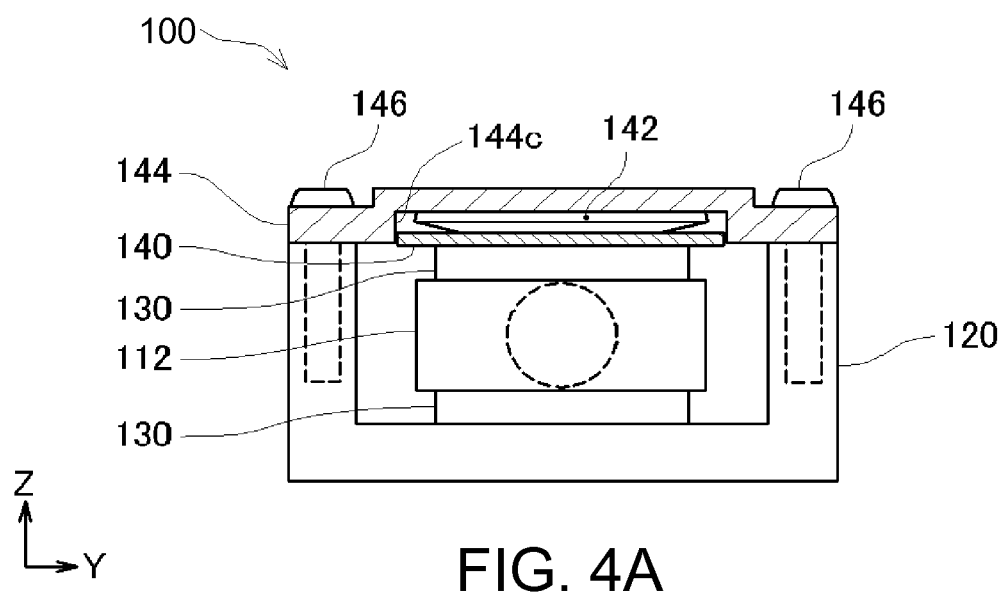
FIGS. 4A and 4B are sectional views showing a method of sandwiching a vibrating body of Embodiment 2.
Figure 4B:
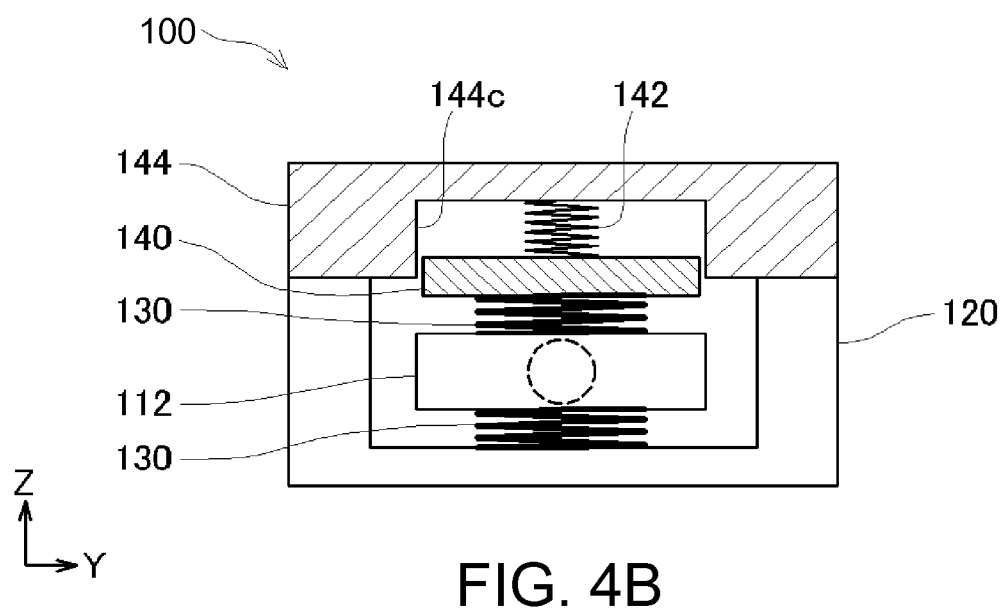

FIG. 4A is an explanatory view showing a structure in which a vibrating body is sandwiched by taking a section in a lateral surface direction of the main portion of this embodiment. FIG. 4B is an explanatory view conceptually showing a structure in which a vibrating body is sandwiched. The section in the lateral surface direction is the section of a sectional side view taken along a surface parallel to a plane including the Y axis and the Z axis.

In this embodiment, the structure in the thickness direction (the direction of the Z axis) of the piezoelectric motor 10 will be described in detail. The device configuration, operation principle, planar structure, and the like of the piezoelectric motor 10 are the same as the description in Embodiment 1, thus overlapping description of the common constituent portions and operation will not be repeated.

Sandwiching Structure of Vibrating Body

As shown in FIG. 4A, the vibrating body 112 is stored in the vibrating body case 120 in a state where both sides in the direction of the Z axis are sandwiched by the buffer portions 130. The buffer portions 130 are secured to the vibrating body 112 by an adhesive. The pressing plate 140, the disk spring 142, and the pressing lid 144 are placed from above the vibrating body 112 and the buffer portions 130 accommodated in the vibrating body case 120, and the pressing lid 144 is attached to the vibrating body case 120 by the locking screws 146.

A concave portion 144c is formed on the inner surface side of the pressing lid 144 (the side toward the vibrating body 112), and if the pressing lid 144 is attached to the vibrating body case 120 by the locking screws 146, the disk spring 142 is compressed and the upper surface of the pressing plate 140 is fit into the concave portion 144c. If the pressing lid 144 is attached to the vibrating body case 120 by the locking screws 146, the disk spring 142 is compressed in the Z direction, and the buffer portions 130 are compressed in the Z direction. However, rigidity of the disk spring 142 in the Z direction is set to a value sufficiently smaller than rigidity of the buffer portions 130 in the Z direction.

FIG. 4B conceptually shows a mode in which the vibrating body 112 is sandwiched in the vibrating body case 120. In FIG. 4B, the buffer portions 130 having large rigidity are represented by a large spring, and the disk spring 142 having small rigidity is represented by a small spring. The locking screw 146 is not shown. As shown in the drawing, the piezoelectric motor 10 has a structure in which both sides of the vibrating body 112 are sandwiched by the buffer portions 130 having large rigidity, and the entire structure (the vibrating body 112 and the buffer portions 130 on both sides) is pressed against the vibrating body case 120 through the pressing plate 140 by the disk spring 142 having rigidity smaller than the buffer portions 130 and retained. In a state where at least the main portion 100 is assembled, since the upper surface of the pressing plate 140 is fit into the concave portion 144c, the pressing plate 140 is in a state where movement in the vibration direction (X direction and Y direction) of the vibrating body 112 is restricted. In this way, for example, even when large variation in dimension occurs in the thickness direction (Z direction) of the vibrating body 112 or the buffer portions 130, the vibrating body 112 can be stored in the vibrating body case 120 in a state of being appropriately retained by the buffer portions 130. Hereinafter, this point will be described in detail.

Figure 5A:
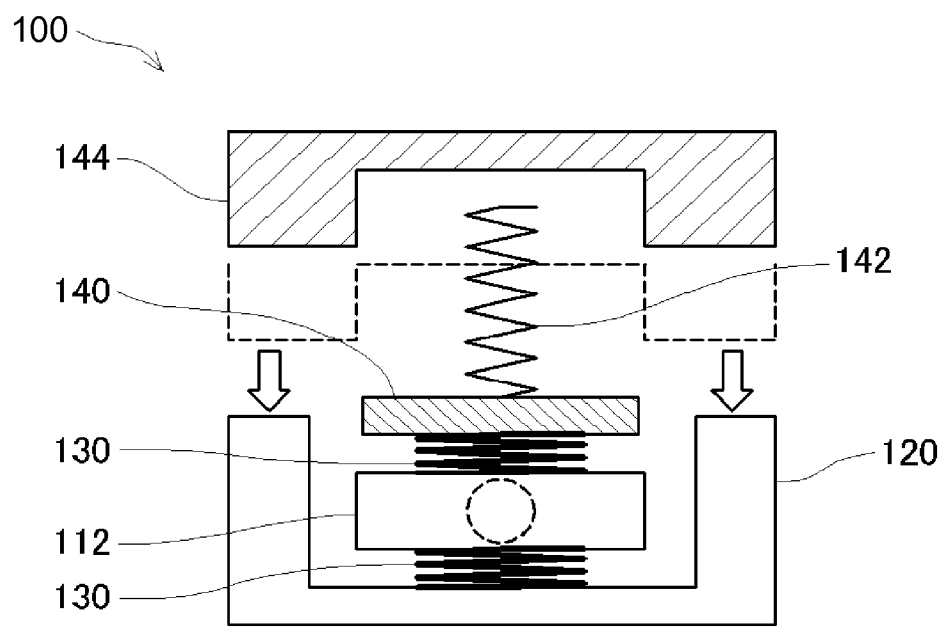
FIGS. 5A and 5B are explanatory views relating to a method of sandwiching a vibrating body.
Figure 5B:
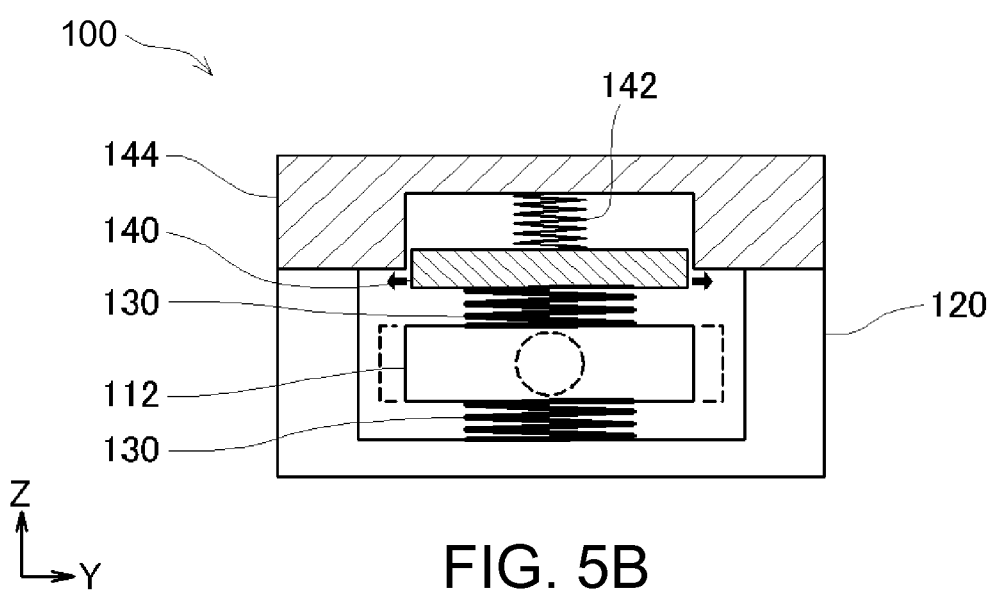

FIGS. 5A and 5B are explanatory views showing a mode in which the vibrating body 112 and the buffer portions 130 are mounted in the vibrating body case 120. FIG. 5A shows a state before the pressing lid 144 is attached to the vibrating body case 120, and FIG. 5B shows a state where the pressing lid 144 is attached to the vibrating body case 120 by the locking screws 146 (not shown). In a state before the pressing lid 144 is attached to the vibrating body case 120, a compression force is not applied to the disk spring 142 and the buffer portions 130. From this state, if the pressing lid 144 is pressed against the vibrating body case 120 by the locking screws 146 (not shown), a compression force is applied to the disk spring 142 and the buffer portions 130.

Meanwhile, as described above, rigidity of the disk spring 142 is set to be smaller than rigidity of the buffer portions 130. For this reason, even when a force of the same magnitude is applied to the disk spring 142 and the buffer portions 130, the buffer portions 130 are hardly deformed, and the disk spring 142 is deformed alone. As a result, in a state where the pressing lid 144 is attached to the vibrating body case 120, as shown in FIG. 5B, the buffer portions 130 hardly contract, and the disk spring 142 contracts alone. At this time, a force when the buffer portions 130 are pressed against the vibrating body 112 becomes equal to the compression force applied to the disk spring 142 (the force which contracts the disk spring 142).

If the vibrating body 112 and the buffer portions 130 vary in dimension, since the amount of compression of the disk spring 142 changes, the compression force of the disk spring 142, that is, the force when the buffer portion 130 is pressed against the vibrating body 112 also changes. However, as shown in FIGS. 5A and 5B, since the disk spring 142 is used in a largely compressed state, even when the amount of compression of the disk spring 142 changes due to variation in dimension of the vibrating body 112 and the buffer portions 130, the ratio of change with respect to the total amount of compression is merely slight. For this reason, even when variation in dimension occurs in the vibrating body 112 and the buffer portions 130, it becomes possible to avoid variation in the force when the buffer portions 130 are pressed against the vibrating body 112.

This can be considered as follows. That is, a case where a certain variation in dimension occurs in the vibrating body 112 and the buffer portions 130, and the variation in dimension is absorbed by deformation of the buffer portions 130 or the disk spring 142 is considered. Since the buffer portions 130 have large rigidity, if variation in dimension will be absorbed by deformation of the buffer portions 130, the compression force largely changes. In contrast, if the disk spring 142 has rigidity smaller than the buffer portions 130, even when the variation in dimension of the same magnitude is absorbed, the compression force changes slightly. For this reason, if the disk spring 142 having rigidity smaller than the buffer portions 130 is provided, there is no effect of variation in dimension of the vibrating body 112 or the buffer portions 130, making it possible to press the buffer portions 130 against the vibrating body 112 constantly with an appropriate force.

Further, even when a location (in this embodiment, the disk spring 142) having rigidity smaller than the buffer portions 130 is provided, if a force in the shearing direction is applied to the buffer portions 130 with the reaction force when driving the object, the location having small rigidity is deformed, the vibrating body 112 moves with the reaction force when driving the object. However, in this embodiment, as described above with reference to FIGS. 4A and 4B, the pressing plate 140 is fit into the concave portion 144c. For this reason, as shown in FIG. 5B, even when the disk spring 142 is deformed in the shearing direction with the reaction force from the object, the pressing plate 140 interferes with the pressing lid 144. As a result, the disk spring 142 is not shear-deformed, and it becomes possible to stably retain the vibrating body 112 with rigidity in the shearing direction of the buffer portions 130.

As described above in detail, in the piezoelectric motor 10 of this embodiment, for example, even when large variation in dimension occurs in the vibrating body 112 and the buffer portions 130, variation in dimension can be absorbed by deformation of the disk spring 142 between the pressing plate 140 and the pressing lid 144. For this reason, even when a complicated operation to actually measure the dimension in the thickness direction (Z direction) of the vibrating body 112 or the buffer portions 130 and to select and assemble the buffer portions 130 for the vibrating body 112 is not performed, the vibrating body 112 can be accommodated in the vibrating body case 120 in a state where the buffer portions 130 are pressed against the vibrating body 112 with an appropriate force. As a result, it becomes possible to easily manufacture the piezoelectric motor 10. Even when the buffer portions 130 are pressed against the vibrating body 112 by the disk spring 142 having small rigidity, it becomes possible to stably retain the vibrating body 112 with rigidity of the buffer portions 130 with respect to the reaction force when driving the object.

Both sides of the vibrating body 112 are sandwiched by the buffer portions 130 from the direction intersecting the bending direction of the vibrating body 112 in a state of being accommodated in the vibrating body case 120. For this reason, the vibration of the vibrating body 112 is hardly transmitted to the vibrating body case 120, and a loss of the driving force is reduced, thereby efficiently driving the object.

Modifications

The piezoelectric motor 10 of Embodiment 2 has various modifications. Hereinafter, certain modifications will be simply described. In the following modifications, a description will be provided focusing on portions that are different from the piezoelectric motor 10. The same portions as those in the piezoelectric motor 10 are represented by the same reference numerals, and a description thereof will be omitted.

First Modification

Figure 6:
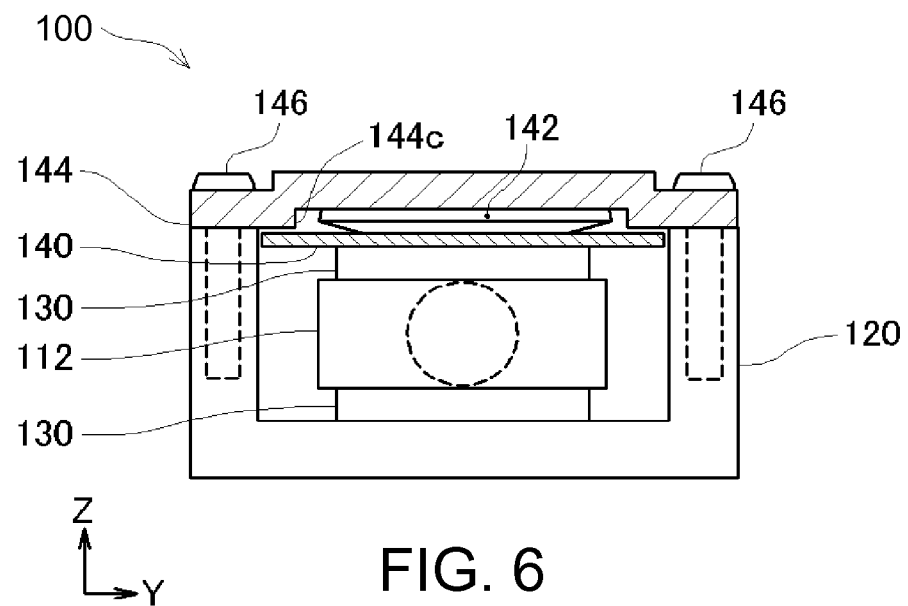
FIG. 6 is a sectional view showing a method of sandwiching a vibrating body in a modification.

In Embodiment 2, a case where the pressing plate 140 is fit into the concave portion 144c of the pressing lid 144, such that the movement of the pressing plate 140 in the X direction or the Y direction is restricted has been described. However, if the movement of the pressing plate 140 in the X direction or the Y direction is restricted, the pressing plate 140 is not necessarily fit into the concave portion 144c. For example, as shown in FIG. 6, the pressing plate 140 may interfere with the inner wall surface of the vibrating body case 120, such that the movement of the pressing plate 140 in the X direction or the Y direction may be restricted. Alternatively, a convex portion protruding from the pressing lid 144 may be fit into a concave portion provided in the pressing plate 140.

Second Modification

Figure 7:
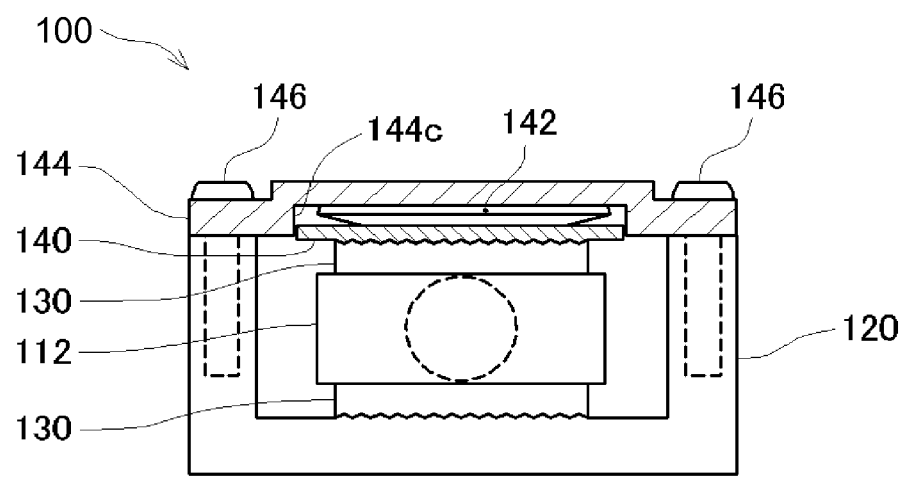
FIG. 7 is a sectional view showing a method of sandwiching a vibrating body in a modification.

In Embodiment 2, a case where the pressing plate 140 is simply pressed against the buffer portions 130 has been described. However, as shown in FIG. 7, unevenness may be provided in the surface of a portion where the pressing plate 140 and each buffer portion 130 are in contact with each other on the pressing plate 140 side (or the buffer portion 130 side). For example, by pressing from the disk spring 142, unevenness provided in the surface of the pressing plate 140 bite into the surface of the buffer portion 130 made of polyimide resin, or unevenness may be provided in the surfaces of the pressing plate 140 and the buffer portion 130 and unevenness may bite/grip each other.

In this way, if the piezoelectric motor 10 is used over a long period, it becomes possible to reliably avoid slipping of the buffer portions 130 between the pressing plate 140 and the buffer portions 130 (or the buffer portions 130 and the vibrating body case 120). Of course, unevenness may be provided in the contact surfaces of the buffer portions 130 and the vibrating body case 120 as well as the contact surfaces of the pressing plate 140 and the buffer portions 130 on the vibrating body case 120 side. Therefore, it becomes possible to prevent the buffer portions 130 from slipping on the contact surfaces of the buffer portions 130 and the vibrating body case 120.

Embodiment 3

Figure 8:
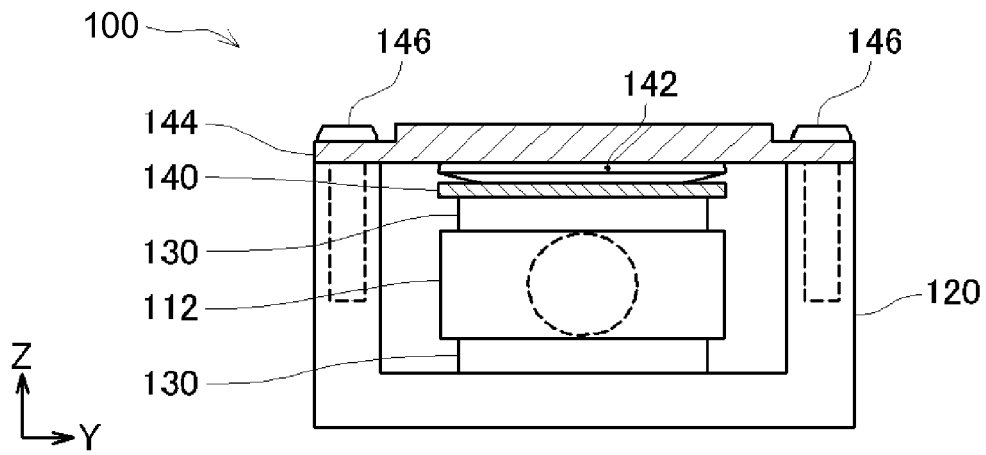
FIG. 8 is an explanatory view relating to a method of sandwiching a vibrating body in Embodiment 3.

FIG. 8 is an explanatory view showing a structure in which a vibrating body is sandwiched by taking a side section of the main portion of this embodiment.

In this embodiment, the structure in the thickness direction (the direction of the Z axis) of the piezoelectric motor 10 different from Embodiment 2 will be described. The device configuration, operation principle, planar structure (side pressure spring attachment structure), and the like of the piezoelectric motor 10 are the same as the description in Embodiment 1, thus overlapping description of the common constituent portions and operation will not be repeated.

Vibrating Body Sandwiching Structure

As shown in FIG. 8, the vibrating body 112 is accommodated in the vibrating body case 120 in a state where both sides in the Z direction are sandwiched by the buffer portions 130. The pressing plate 140, the disk spring 142, and the pressing lid 144 are placed from above the vibrating body 112 and the buffer portions 130 accommodated in the vibrating body case 120, and the pressing lid 144 is attached to the vibrating body case 120 by the locking screws 146. The buffer portions 130 are secured to the vibrating body 112 by an adhesive. In this way, it becomes possible to easily accommodate the vibrating body 112 in the vibrating body case 120 in a state where the vibrating body 112 and the buffer portions 130 in which manufacturing variation is liable to occur are superimposed. Hereinafter, the reason will be described.

Figure 9A:
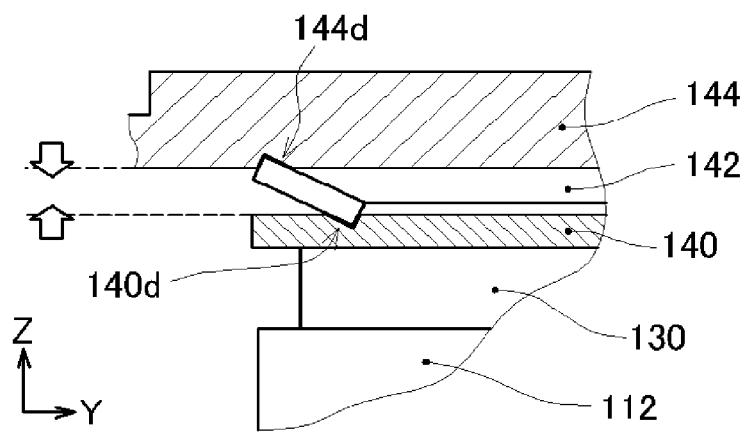
FIGS. 9A and 9B are explanatory views showing a reason why a vibrating body can be appropriately sandwiched while absorbing dimensional variations in a thickness direction of a vibrating body and a buffer portion.
Figure 9B:
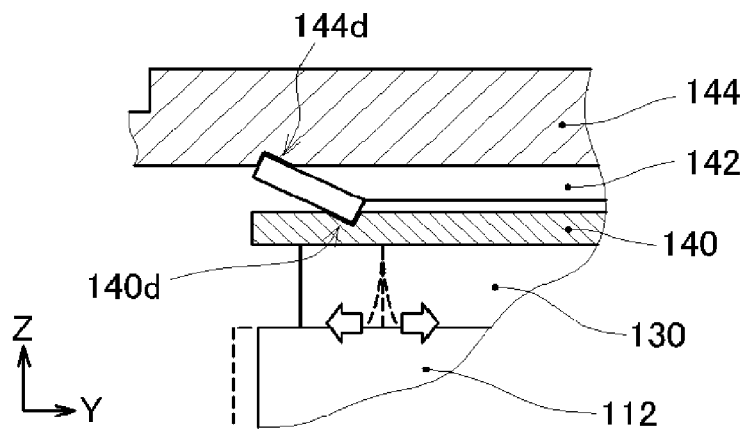

FIGS. 9A and 9B are explanatory views showing the reason why the vibrating body 112 is accommodatable in the vibrating body case 120 in a state where the vibrating body 112 and the buffer portions 130 in which manufacturing variation is liable to occur are superimposed. While the vibrating body 112, the buffer portions 130, the pressing plate 140, and the disk spring 142 are accommodated in the vibrating body case 120 by the pressing lid 144, and of these, the vibrating body 112 or the pressing plate 140 is hardly deformed in the Z direction. Accordingly, variation in dimension in the thickness direction (Z direction) due to manufacturing variation of the vibrating body 112 or the buffer portions 130 should be absorbed by compressive deformation in the remaining portions (the buffer portions 130 and the disk spring 142). Since the vibrating body 112 or the pressing plate 140 is hardly deformed in the vibration direction (Y direction and X direction) of the vibrating body 112, it is desired that the motion of vibration of the vibrating body 112 is absorbed by shear deformation in the remaining portions (the buffer portions 130 or the disk spring 142). Nevertheless, the buffer portions 130 or the disk spring 142 should support the reaction force received by the vibrating body 112 when driving the object.

FIG. 9A is an explanatory view showing a mode in which variation in dimension in the thickness direction (Z direction) due to manufacturing variation of the vibrating body 112 or the buffer portions 130 is absorbed by illustrating a portion where the pressing lid 144, the disk spring 142, and the pressing plate 140 are superimposed on a magnified scale. Since the disk spring 142 operates as a spring with respect to compression in the thickness direction (Z direction), rigidity is smaller than the buffer portions 130. For this reason, for example, even when the vibrating body 112 and the buffer portions 130 vary in dimension in the thickness direction (Z direction), the disk spring 142 is bent in the Z direction, thereby absorbing variation in dimension in the thickness direction.

When the disk spring 142 is compressed between the pressing plate 140 and the pressing lid 144, the corner portion of the disk spring 142 is pressed against the pressing plate 140 and the pressing lid 144. For this reason, a portion against which the corner of the disk spring 142 is pressed is dented to form a first groove 140d in the surface of the pressing plate 140. Similarly, a portion against which the corner of the disk spring 142 is pressed is dented to form a second groove 144d in the surface of the pressing lid 144. While the first groove 140d and the second groove 144d have no relation to the motion of the disk spring 142 for absorbing variation in dimension in the thickness direction, the first groove 140d and the second groove 144d effectively function when absorbing the vibration of the vibrating body 112 or receiving the reaction force from the object.

FIG. 9B shows a mode in which the buffer portions 130 and the disk spring 142 support the reaction force from the object while absorbing the vibration of the vibrating body 112. The disk spring 142 has small rigidity with respect to compression in the thickness direction (Z direction) and has large rigidity with respect to shear deformation in the shearing direction (Y direction or X direction). Since the upper and lower-side corners of the disk spring 142 are fit into the second groove 144d of the pressing lid 144 and the first groove 140d of the pressing plate 140, there is no case where the disk spring 142 slips with respect to the pressing plate 140 or the pressing lid 144. Accordingly, in regard to the motion of the vibrating body 112 in the Y direction (or the X direction), a portion from the pressing plate 140 to the pressing lid 144 may be substantially regarded as a rigid body. For this reason, the vibration of the vibrating body 112 is absorbed by shear deformation of the buffer portions 130 alone. The reaction force received from the object is supported by shear deformation of the buffer portions 130 alone.

The first groove 140d of the pressing plate 140 or the second groove 144d of the pressing lid 144 has a function such that the disk spring 142 does not slip. Accordingly, it should suffice that the groove becomes a "hook" when the disk spring 142 slips, and as illustrated in FIGS. 9A and 9B, a clear dent may not be formed. For example, even when a small dent made of a slight scratch in the surface is provided, this functions as the "hook" when the disk spring 142 slips, and thus corresponds to the first groove 140d or the second groove 144d of this embodiment.

As will be apparent from the above description, the disk spring 142 provided between the pressing plate 140 and the pressing lid 144 functions as a spring having rigidity smaller than the buffer portions 130 in the direction (Z direction) in which the buffer portions 130 are pressed against the vibrating body 112. For this reason, for example, even when large variation in dimension in the thickness direction (Z direction) occurs due to manufacturing variation of the vibrating body 112 and the vibrating body case 120, the variation in dimension can be absorbed by the disk spring 142. As a result, the vibrating body 112 can be simply accommodated in the vibrating body case 120 without a complicated operation to select and assemble the vibrating body 112 and the vibrating body case 120 by dimension in the thickness direction (Z direction). Since the portion from the pressing plate 140 to the pressing lid 144 substantially operates as a rigid body in the vibration direction (Y direction or X direction) of the vibrating body 112 or the direction (primarily, the Y direction) in which the reaction force from the object is received, there is no effect of the disk spring 142. For this reason, there is no adverse effect on the function of the buffer portions 130 of absorbing the vibration of the vibrating body 112 and supporting the reaction force from the object. As a result, according to the sandwiching structure of the vibrating body 112 of this embodiment, there is no adverse effect from the viewpoint of performance, and it becomes possible to easily manufacture the piezoelectric motor 10.

Both sides of the vibrating body 112 are sandwiched by the buffer portions 130 from the direction intersecting the bending direction of the vibrating body 112 in a state of being accommodated in the vibrating body case 120. For this reason, the vibration of the vibrating body 112 is not easily transmitted to the vibrating body case 120, and a loss of the driving force is reduced, thereby efficiently driving the object.

Figure 10:
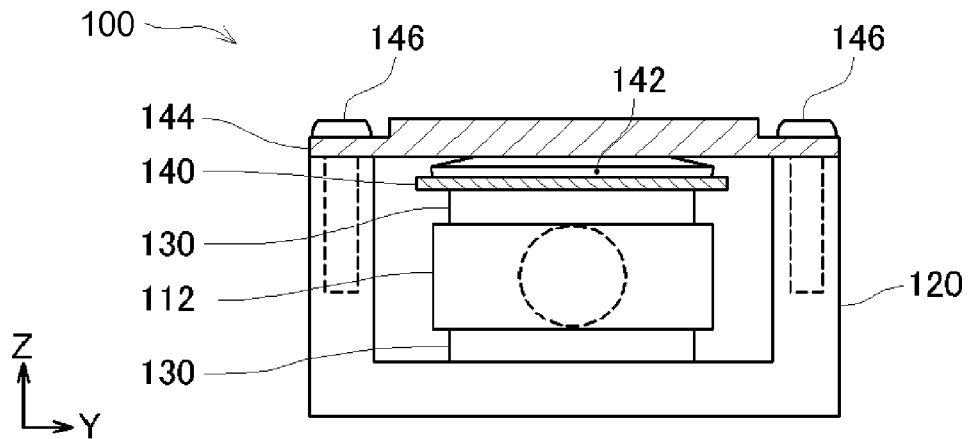
FIG. 10 is an explanatory view showing another form of a method of sandwiching a vibrating body.

As will be apparent from the above description, it should suffice that the disk spring 142 is provided between the pressing plate 140 and the pressing lid 144. Accordingly, as shown in FIG. 10, the direction of the disk spring 142 may be reversed vertically.

Modifications

The piezoelectric motor 10 of Embodiment 3 has various modifications. Hereinafter, certain modifications will be simply described. In the following modifications, a description will be provided focusing on portions that are different from the piezoelectric motor 10. The same portions as those in the piezoelectric motor 10 are represented by the same reference numerals, and a description thereof will be omitted.

Third Modification

In Embodiment 3, although the first groove 140d or the second groove 144d is not formed in the pressing plate 140 or the pressing lid 144 before assembling, a case where the pressing plate 140 or the pressing lid 144 is pressed against the disk spring 142 during assembling, and the corner of the disk spring 142 bites into the pressing plate 140 or the pressing lid 144 to form the first groove 140d of the pressing plate 140 or the second groove 144d of the pressing lid 144 has been described.

However, the first groove 140d or the second groove 144d may be formed in the surface of the pressing plate 140 or the pressing lid 144 in advance. In this way, as the material for the pressing plate 140 or the pressing lid 144, a material (for example, a material whose surface is subjected to thermal treatment), which is harder than the disk spring 142 and has resistance to abrasion, or the like may be used. If the first groove 140d or the second groove 144d is deeply formed, the disk spring 142 can be more stably retained with respect to the pressing plate 140 or the pressing lid 144, thereby reliably preventing the disk spring 142 from slipping.

Fourth Modification

In Embodiment 3 and the foregoing modification, a case where the disk spring 142 is simply sandwiched between the pressing plate 140 and the pressing lid 144 has been described. However, a concave portion may be formed in at least one of the pressing plate 140 and the pressing lid 144, and the outer circumferential portion of the disk spring 142 may be fit into the concave portion.

Figure 11A:
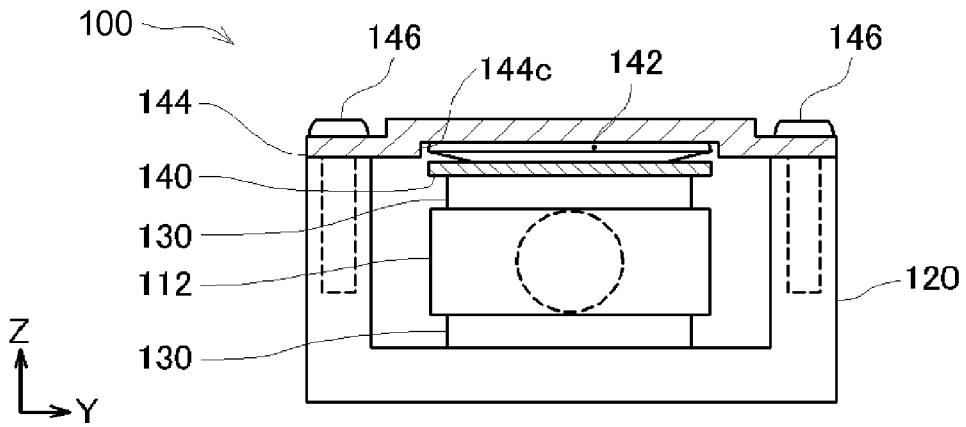
FIGS. 11A and 11B are explanatory views showing a method of sandwiching a vibrating body in a modification.
Figure 11B:
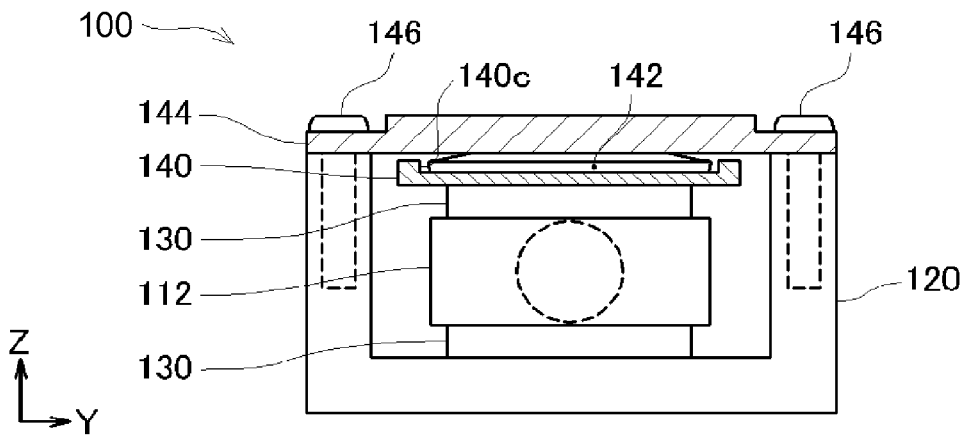

FIGS. 11A and 11B are sectional views showing a sandwiching structure of a fourth modification. In the example shown in FIG. 11A, a concave portion 144c is formed in the pressing lid 144, and the disk spring 142 is loosely fit into the concave portion 144c. In the example shown in FIG. 11B, a concave portion 140c is formed in the pressing plate 140, and the disk spring 142 is loosely fit into the concave portion 140c. In this way, when the pressing plate 140, the disk spring 142, and the pressing lid 144 are superimposed and assembled in the vibrating body case 120, there is no case where the disk spring 142 largely moves, thereby facilitating the assembling operation.

The concave portion 140c formed in the pressing plate 140 or the concave portion 144c formed in the pressing lid 144 may have a shape such that the outer circumferential portion of the disk spring 142 is fit therein. Accordingly, while the shape of the outer circumference when the disk spring 142 is viewed from the compression direction (Z direction) is a circular shape, the shape of the concave portion 140c or the concave portion 144c when viewed from the compression direction (Z direction) is not limited to a circular shape, and a polygonal shape, such as a square shape, may be used.

In the above description, a case where the disk spring 142 is loosely fit into the concave portion 140c or the concave portion 144c has been described. Accordingly, until the disk spring 142 is assembled between the pressing plate 140 and the pressing lid 144 and receives the compression force, the disk spring 142 can slightly move in the concave portion 140c or the concave portion 144c. However, the outer circumferential portion of the disk spring 142 may be fit such that the disk spring 142 does not move in the concave portion 140c or the concave portion 144c. In this way, it becomes possible to easily assemble the disk spring 142, and to reliably prevent the disk spring 142 from slipping with respect to the pressing plate 140 or the pressing lid 144 due to the vibration of the vibrating body 112 or the reaction force received from the object during the operation of the piezoelectric motor 10.

Fifth Modification

In the fourth modification, a case where the outer circumferential portion of the disk spring 142 is fit into the concave portion 140c of the pressing plate 140 or the concave portion 144c of the pressing lid 144 has been described. In contrast, the inner circumferential portion of the disk spring 142 may be fit into a convex portion protruding from the pressing plate 140 or the pressing lid 144.

Figure 12A:
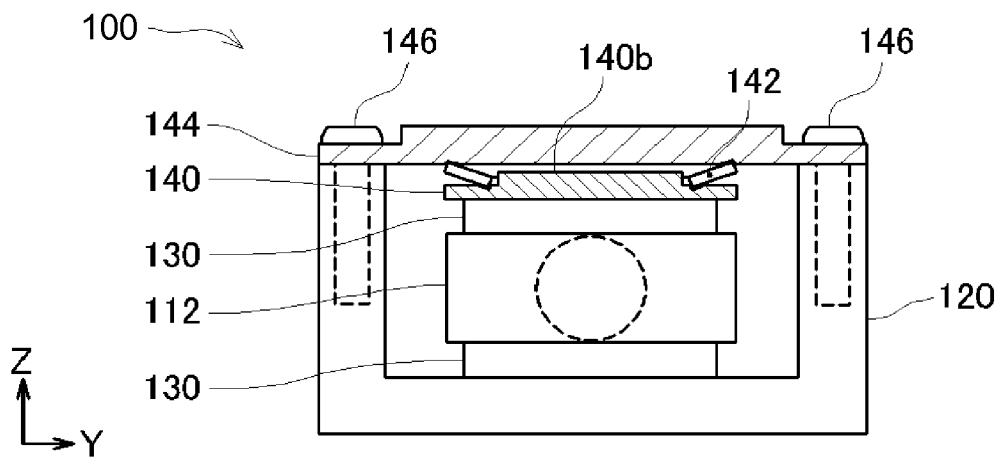
FIGS. 12A and 12B are explanatory views showing a method of sandwiching a vibrating body in a modification.
Figure 12B:
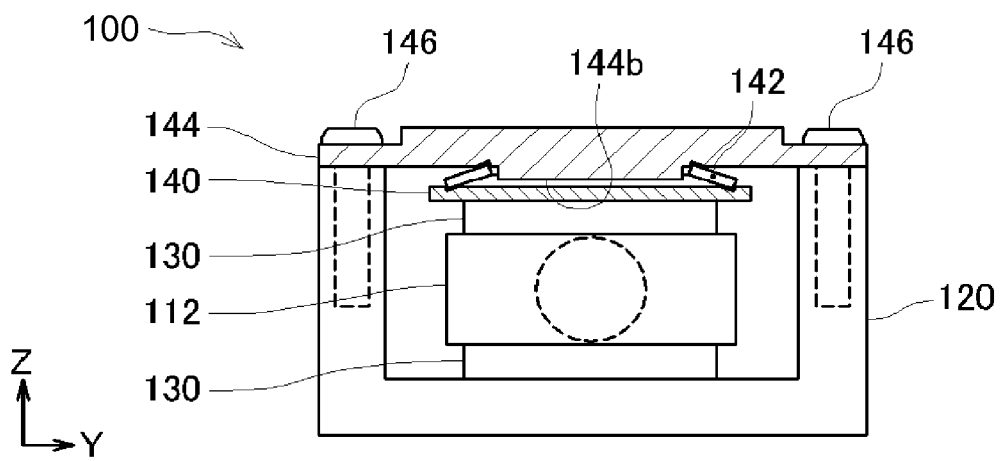

FIGS. 12A and 12B are sectional views showing a sandwiching structure of a fifth modification. In the example shown in FIG. 12A, a convex portion 140b is provided to protrude from the pressing plate 140, and the inner circumferential portion of the disk spring 142 is loosely fit into the convex portion 140b. In the example shown in FIG. 12B, a convex portion 144b is provided to protrude from the pressing lid 144, and the inner circumferential portion of the disk spring 142 is loosely fit into the convex portion 144b. In this way, when the pressing plate 140, the disk spring 142, and the pressing lid 144 are superimposed and assembled in the vibrating body case 120, there is no case where the disk spring 142 largely moves, thereby facilitating the assembling operation.

The convex portion 140b of the pressing plate 140 or the convex portion 144b of the pressing lid 144 may have a shape such that the inner circumferential portion of the disk spring 142 is fit therein. Accordingly, while the inner circumference shape of the disk spring 142 is a circular shape when the disk spring 142 is viewed from the compression direction (Z direction), the shape of the convex portion 140b or the convex portion 144b when viewed from the compression direction is not limited to a circular shape, and a polygonal shape, such as a square shape, may be used.

In this modification, a case where the disk spring 142 is loosely fit into the convex portion 140b or the convex portion 144b has been described. Accordingly, even when the disk spring 142 is fit into the convex portion 140b or the convex portion 144b, the disk spring 142 can slightly move. However, the inner circumferential portion of the disk spring 142 may be fit such that the disk spring 142 is fit into the convex portion 140b or the convex portion 144b. In this way, it becomes possible to easily assemble the disk spring 142 and to reliably prevent the disk spring 142 from slipping with respect to the pressing plate 140 or the pressing lid 144 during the operation of the piezoelectric motor 10.

Application Examples

The piezoelectric motor 10 of each embodiment described above can be of small size, can drive the object with high precision, and can be easily manufactured. Therefore, the piezoelectric motor can be suitably incorporated as a driving device of the following device, for example.

Figure 13:
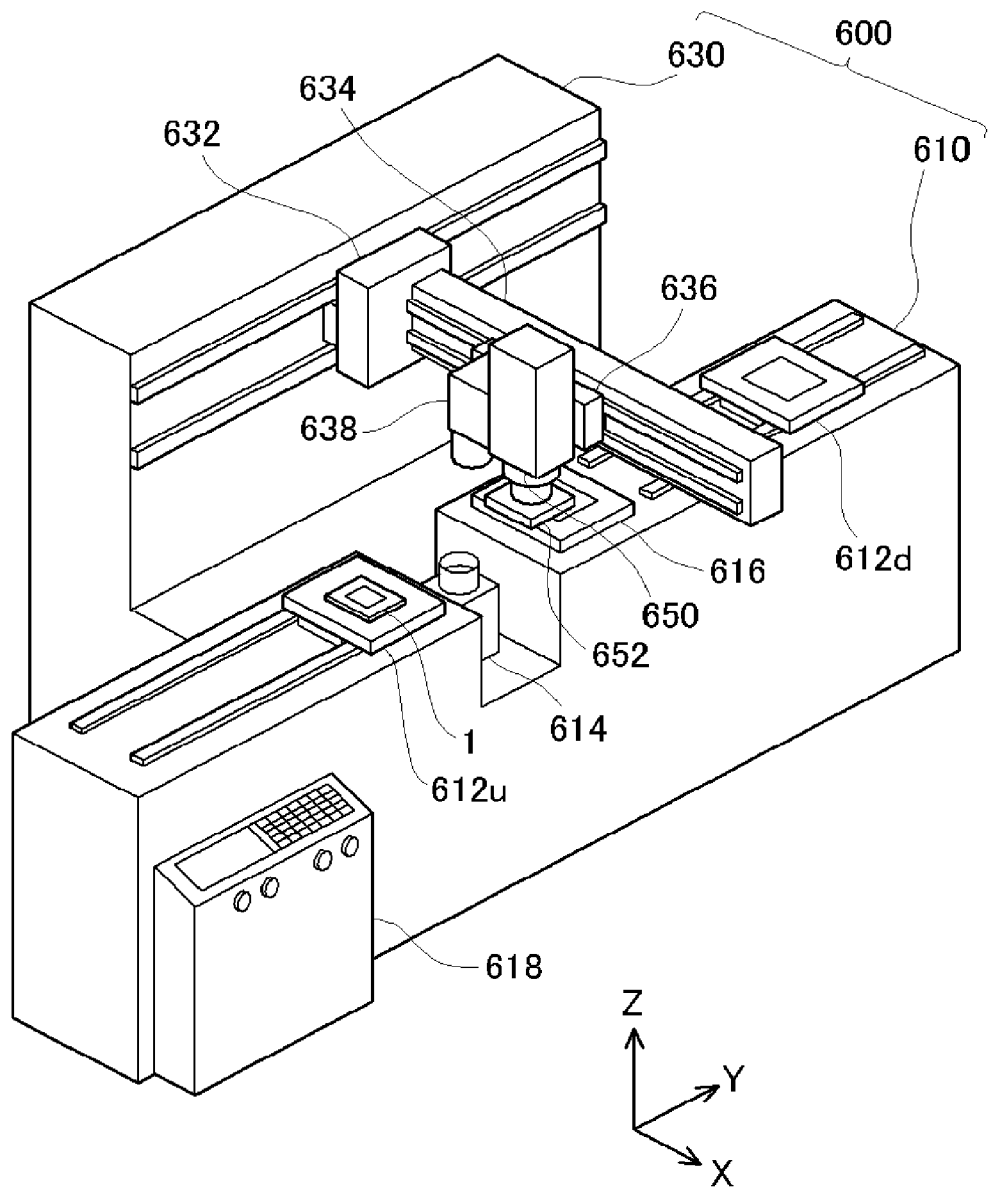
FIG. 13 is a perspective view illustrating an electronic component inspection device embedded with a piezoelectric motor.

FIG. 13 is a perspective view illustrating an electronic component inspection device 600 in which the piezoelectric motor is incorporated. The electronic component inspection device 600 broadly includes a base 610, and a support 630 which is provided upright on the lateral surface of the base 610. On the upper surface of the base 610 are provided an upstream-side stage 612u which is conveyed with an electronic component 1 to be inspected placed thereon, and a downstream-side stage 612d which is conveyed with the inspected electronic component 1 placed thereon. Between the upstream-side stage 612u and the downstream-side stage 612d are provided an imaging device 614 which confirms the posture of the electronic component 1, and an inspection table 616 on which the electronic component 1 is set so as to inspect electrical characteristics. Representative examples of the electronic component 1 include "semiconductors", "display devices, such as CLD or OLED", "crystal devices", "various sensors", "ink jet heads", "various MEMS devices", and the like. The inspection table 616 of this embodiment corresponds to the "inspection socket" according to the invention.

A Y stage 632 is provided in the support 630 to be movable in a direction (Y direction) parallel to the upstream-side stage 612u and the downstream-side stage 612d of the base 610, and an arm portion 634 extends from the Y stage 632 in a direction (X direction) toward the base 610. An X stage 636 is provided on the lateral surface of the arm portion 634 to be movable in the X direction. An imaging camera 638 and a holding device 650 embedded with a Z stage movable in an up-down direction (Z direction) are provided in the X stage 636. A holding portion 652 which holds the electronic component 1 is provided at the tip of the holding device 650. A control unit 618 which controls the overall operation of the electronic component inspection device 600 is provided on the front surface side of the base 610. In this application example, the X stage 636, the Y stage 632, and the Z stage embedded in the holding device 650 correspond to the "moving device" according to the invention.

The electronic component inspection device 600 having the above configuration inspects the electronic component 1 as follows. First, the electronic component 1 to be inspected is placed on the upstream-side stage 612u and moves near the inspection table 616. Next, the Y stage 632 and the X stage 636 are driven to move the holding device 650 to a position directly above the electronic component 1 placed on the upstream-side stage 612u. At this time, the position of the electronic component 1 can be confirmed using the imaging camera 638. The holding device 650 falls using the Z stage embedded in the holding device 650, if the electronic component 1 is held using the holding portion 652, the holding device 650 moves directly above the imaging device 614, and the posture of the electronic component 1 is confirmed using the imaging device 614. Subsequently, the posture of the electronic component 1 is adjusted using a fine adjustment mechanism embedded in the holding device 650. The holding device 650 moves to above the inspection table 616, and then the Z stage embedded in the holding device 650 is driven to set the electronic component 1 on the inspection table 616. Since the posture of the electronic component 1 is adjusted using the fine adjustment mechanism in the holding device 650, it is possible to set the electronic component 1 at a correct position of the inspection table 616. After the electrical characteristics of the electronic component 1 are inspected using the inspection table 616, the electronic component 1 is excluded from the inspection table 616, the Y stage 632 and the X stage 636 are driven to move the holding device 650 to above the downstream-side stage 612d, and the electronic component 1 is placed on the downstream-side stage 612d. Thereafter, the downstream-side stage 612d is driven to convey the inspected electronic component 1 to a predetermined position.

Figure 14:
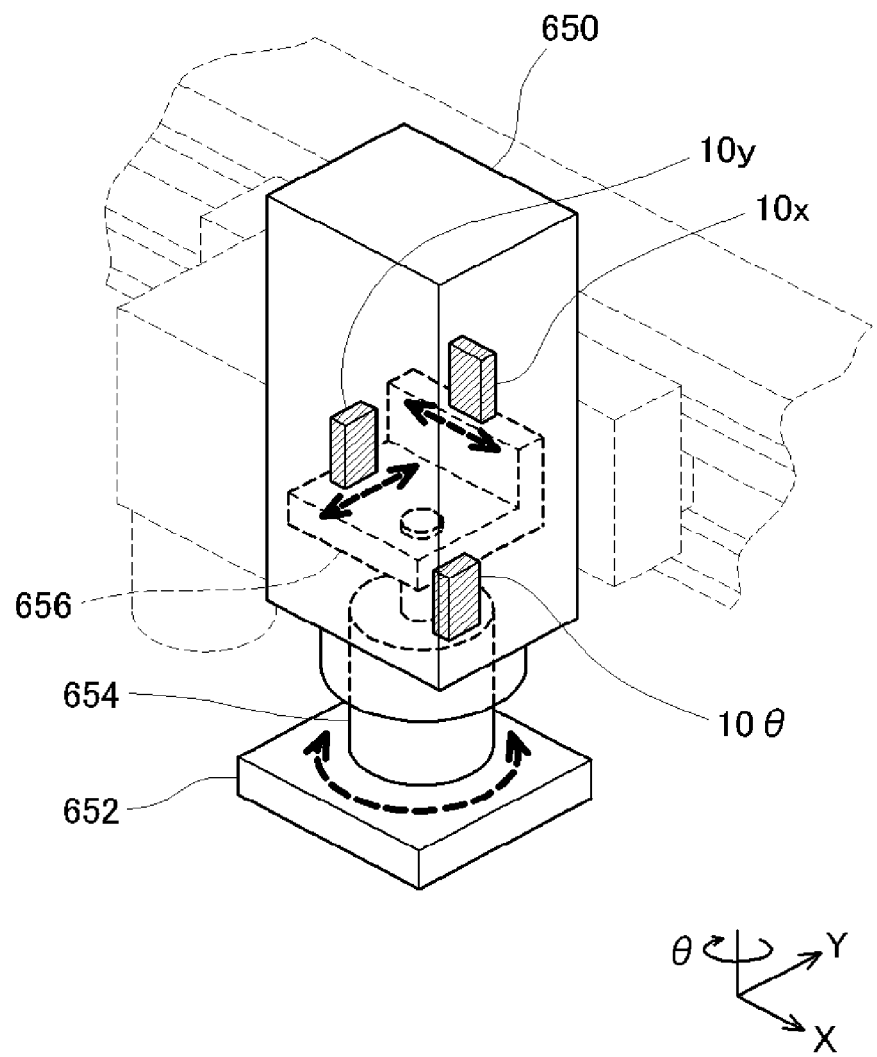
FIG. 14 is an explanatory view of a fine adjustment mechanism embedded in a holding device.

FIG. 14 is an explanatory view of the fine adjustment mechanism embedded in the holding device 650. As shown in the drawing, in the holding device 650 are provided a rotation shaft 654 connected to the holding portion 652, and a fine adjustment plate 656 to which a rotation shaft 654 is rotatably attached. The fine adjustment plate 656 is movable in the X direction and the Y direction using a guide mechanism (not shown).

As indicated by hatching in FIG. 14, a piezoelectric motor 10θ for a rotation direction toward the end surface of the rotation shaft 654 is mounted, and a driving convex portion (not shown) of the piezoelectric motor 10θ is pressed against the end surface of the rotation shaft 654. For this reason, if the piezoelectric motor 10θ is operated, it becomes possible to rotate the rotation shaft 654 (and the holding portion 652) in a θ direction by an arbitrary angle with high precision. A piezoelectric motor 10x for the X direction toward the fine adjustment plate 656 and a piezoelectric motor 10y for the Y direction are provided, and the driving convex portions (not shown) of the piezoelectric motors 10x and 10y are pressed against the surface of the fine adjustment plate 656. For this reason, if the piezoelectric motor 10x is operated, it becomes possible to move the fine adjustment plate 656 (and the holding portion 652) in the X direction by an arbitrary distance with high precision. Similarly, if the piezoelectric motor 10y is operated, it becomes possible to move the fine adjustment plate 656 (and the holding portion 652) in the Y direction by an arbitrary distance with high precision. Accordingly, in the electronic component inspection device 600 of FIG. 13, if the piezoelectric motor 10θ, the piezoelectric motor 10x, and the piezoelectric motor 10y are operated, it is possible to finely adjust the posture of the electronic component 1 held by the holding portion 652. In this application example, the piezoelectric motor 10x and the piezoelectric motor 10y respectively correspond to the "first piezoelectric motor" and "second piezoelectric motor" according to the invention, and the piezoelectric motor 10θ corresponds to the "third piezoelectric motor" according to the invention. The rotation shaft 654 or the fine adjustment mechanism having the fine adjustment plate 656, the piezoelectric motor 10θ, the piezoelectric motor 10x, and the piezoelectric motor 10y corresponds to the "driving device" according to the invention.

Figure 15:
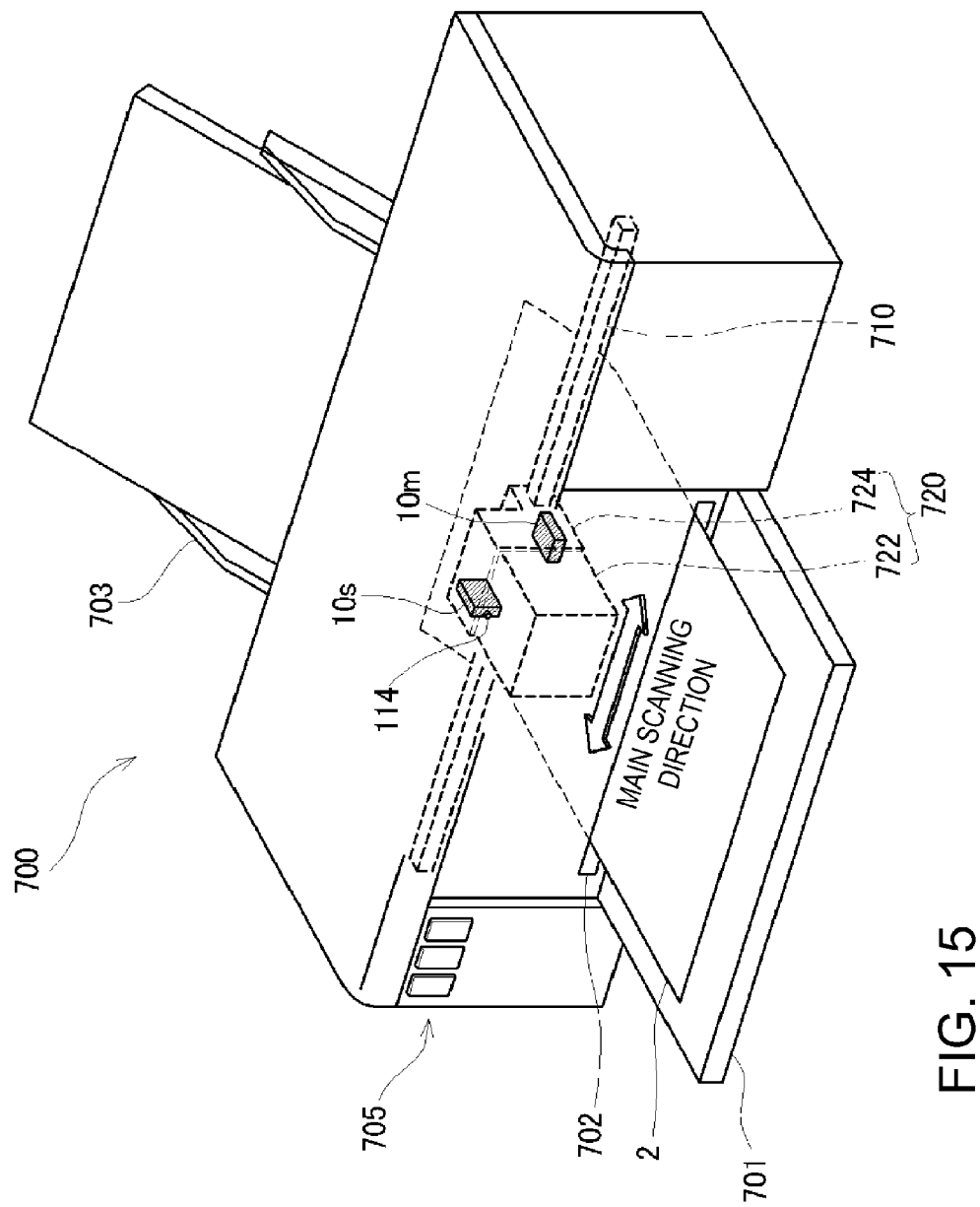
FIG. 15 is a perspective view illustrating a printing device embedded with a piezoelectric motor.

FIG. 15 is a perspective view illustrating a printing device 700 in which the piezoelectric motor 10 of this application example is incorporated. The printing device 700 is a so-called ink jet printer which ejects ink onto the surface of a printing medium 2 to print an image. The printing device 700 substantially has a boxlike appearance shape, and is provided with a sheet discharge tray 701 substantially at the center of the front surface, a discharge port 702, and a plurality of operation buttons 705. A feed tray 703 is provided on the rear surface side. If the printing medium 2 is set in the feed tray 703 and the operation button 705 is operated, the printing medium 2 is drawn from the feed tray 703, an image is printed on the printing medium 2 inside the printing device 700, and the printing medium 2 is discharged from the discharge port 702.

Inside the printing device 700 are provided a carriage 720 which reciprocates in a main scanning direction on the printing medium 2, and a guide rail 710 which guides the movement of the carriage 720 in the main scanning direction. The carriage 720 has an ejection head 722 which ejects ink onto the printing medium 2, a driving unit 724 which drives the carriage 720 in the main scanning direction, and the like. A plurality of ejection nozzles are provided on the bottom surface side (the side toward the printing medium 2) of the ejection head 722, such that ink can be ejected from the ejection nozzles toward the printing medium 2. Piezoelectric motors 10m and 10s are mounted in the driving unit 724. A driving convex portion (not shown) of the piezoelectric motor 10m is pressed against the guide rail 710. For this reason, if the piezoelectric motor 10m is operated, it is possible to move the carriage 720 in the main scanning direction. A driving convex portion 114 of the piezoelectric motor 10s is pressed with respect to the ejection head 722. For this reason, if the piezoelectric motor 10s is operated, the bottom surface side of the ejection head 722 can be close to the printing medium 2 or can be away from the printing medium 2. In the printing device 700 which uses so-called roll paper as the printing medium 2, a mechanism for cutting roll paper with the image printed thereon is required. In this case, if a cutter is attached to the carriage 720 and moved in the main scanning direction, it is possible to cut roll paper.

Figure 16:
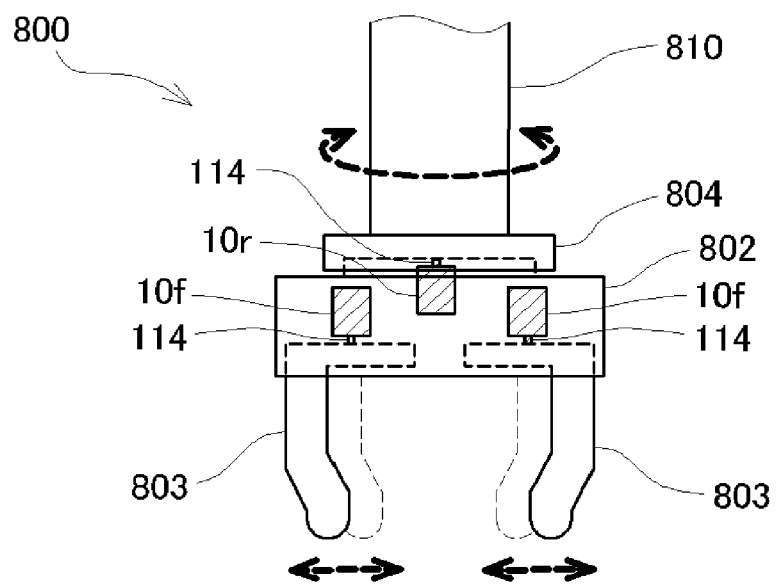
FIG. 16 is an explanatory view illustrating a robot hand embedded with a piezoelectric motor.

FIG. 16 is an explanatory view illustrating a robot hand 800 in which the piezoelectric motor 10 of this application example is incorporated. In the robot hand 800, a plurality of finger portions 803 are provided upright from a base 802, and are connected to an arm 810 through a wrist 804. A root portion of each finger portion 803 is movable in the base 802, and a piezoelectric motor 10f is mounted in a state where a driving convex portion 114 is pressed against the root portion of the finger portion 803. For this reason, if the piezoelectric motors 10f are operated, the finger portions 803 can be moved to hold the object. A piezoelectric motor 10r is mounted in the portion of the wrist 804 in a state where a driving convex portion 114 is pressed against the end surface of the wrist 804. For this reason, if the piezoelectric motor 10r is operated, it is possible to rotate the entire base 802.

Figure 17:
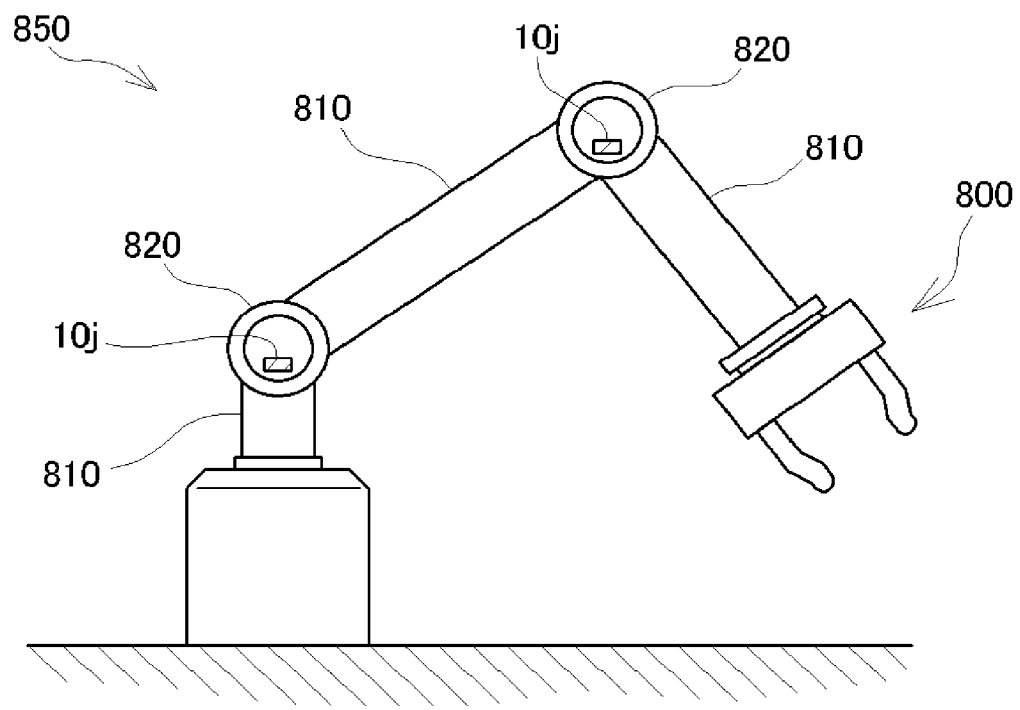
FIG. 17 is an explanatory view illustrating a robot including a robot hand.

FIG. 17 is an explanatory view illustrating a robot 850 including the robot hand 800. As shown in the drawing, the robot 850 includes a plurality of arms 810, and joint portions 820 which connect the arms 810 in a bendable state. The robot hand 800 is connected to the tip of the arm. 810. Each joint portion 820 is embedded with a piezoelectric motor 10j as an actuator for bending the joint portion 820. For this reason, if the piezoelectric motor 10j is operated, it is possible to bend each joint portion 820 by an arbitrary angle.

Although the piezoelectric motor according to embodiments of the invention or various devices having the piezoelectric motor mounted therein have been described, the invention is not limited to the foregoing application examples and modifications, and may be carried out in various forms without departing from the scope of the invention.

The entire disclosures of Japanese Patent Application Nos. 2011-266557 filed Dec. 6, 2011 and 2011-266560 filed Dec. 6, 2011 are expressly incorporated by reference herein.

What is claimed is:

1. A piezoelectric motor in which stretching vibration and bending vibration are generated in a vibrating body to move an object, the piezoelectric motor comprising:
    a vibrating body which contains a piezoelectric material, and has a convex portion protruding from an end surface;
    a case which accommodates the vibrating body;
    a pressing elastic body which presses the case in a direction bringing the convex portion of the vibrating body into contact with the object;
    buffer portions which sandwich both sides of the vibrating body from a direction intersecting a bending direction of the vibrating body in the case, and contain a material having dynamic viscoelasticity;
    pressing lids which are attached to the case;
    disk springs which are provided between the pressing lids and the buffer portions, and are compressed by the pressing lids; and
    pressing plates which are provided between the buffer portions and the disk springs to restrict movement in a stretching direction and a bending direction of the vibrating body.

2. The piezoelectric motor according to claim 1, wherein the pressing plates are fit into the pressing lids.

3. The piezoelectric motor according to claim 1, wherein the pressing plates have uneven contact surfaces contacting the buffer portions.

4. The piezoelectric motor according to claim 1, wherein the buffer portions have uneven contact surfaces contacting the pressing plates.

5. A driving device comprising:
the piezoelectric motor according to claim 1.

6. A printing device comprising:
the piezoelectric motor according to claim 1.

7. A robot hand comprising:
the piezoelectric motor according to claim 1.

8. A robot comprising:
the robot hand according to claim 7.

9. An electronic component inspection device which mounts a held electronic component in an inspection socket, and inspects the electrical characteristics of the electronic component,
    wherein the electronic component is aligned with respect to the inspection socket by the piezoelectric motor according to claim 1.

10. An electronic component conveying device which conveys a held electronic component, wherein the electronic component is aligned by the piezoelectric motor according to claim 1.

11. An electronic component conveying device comprising:
- a holding device which holds an electronic component;
- a moving device which moves the holding device in directions of three axes in total of a first axis and a second axis perpendicular to each other and a third axis perpendicular to the first axis and the second axis; and
- a control device which controls the operation of the moving device,
- wherein the holding device is embedded with a first piezoelectric motor which moves the electronic component in the direction of the first axis, a second piezoelectric motor which moves the electronic component in the direction of the second axis, and a third piezoelectric motor which rotates the electronic component around the third axis,
- the first to third piezoelectric motors are the piezoelectric motor according to claim 1.

12. An electronic component inspection device comprising:
- an inspection socket in which an electronic component is mounted, and the electrical characteristics of the electronic component are inspected;
- a holding device which holds the electronic component;
- a moving device which moves the holding device in directions of three axes in total of a first axis and a second axis perpendicular to each other and a third axis perpendicular to the first axis and the second axis;
- an imaging device which is provided on the first axis or the second axis when viewed from the inspection socket to detect a posture of the electronic component mounted in the inspection socket;
- an upstream-side stage which conveys the electronic component from the inspection socket to a predetermined position on the first axis or the second axis connecting the imaging device;
- a downstream-side stage which conveys the electronic component from a predetermined position opposite to the side on which the imaging device is provided when viewed from the inspection socket; and
- a control device which controls the operation of the moving device,
- wherein the control device includes:
  - a first control unit which moves the holding device holding the electronic component conveyed by the upstream-side stage onto the imaging device,
  - a second control unit which moves the holding device to mount the electronic component whose posture is confirmed by the imaging device in the inspection socket, and
  - a third control unit which moves the holding device to place the electronic component whose electrical characteristics are inspected in the inspection socket from the inspection socket to the downstream-side stage,
- the holding device is embedded with a first piezoelectric motor which moves the electronic component in the direction of the first axis on the basis of the posture of the electronic component detected by the imaging device, a second piezoelectric motor which moves the electronic component in the direction of the second axis on the basis of the posture of the electronic component detected by the imaging device, and a third piezoelectric motor which rotates the electronic component around the third axis on the basis of the posture of the electronic component detected by the imaging device, and
- the first to third piezoelectric motors are the piezoelectric motor according to claim 1.

13. A piezoelectric motor in which stretching vibration and bending vibration are generated in a vibrating body to move an object, the piezoelectric motor comprising:
- a vibrating body which contains a piezoelectric material, and has a convex portion protruding from an end surface,
- a case which accommodates the vibrating body;
- a pressing elastic body which presses the case in a direction bringing the convex portion of the vibrating body into contact with the object;
- buffer portions which sandwich both sides of the vibrating body from a direction intersecting a bending direction of the vibrating body in the case, and are contain a material having dynamic viscoelasticity;
- pressing lids which are attached to the case;
- disk springs which are compressed by the pressing lids;
- pressing plates which are provided between the disk springs and the buffer portions.

14. The piezoelectric motor according to claim 13,
- wherein each pressing plate has a first groove into which a corner portion of the corresponding disk spring coming into contact with the pressing plate is fit, and
- each pressing lid has a second groove into which a corner portion of the corresponding disk spring coming into contact with the pressing lid is fit.

15. The piezoelectric motor according to claim 13,
- wherein a concave portion into which an outer circumferential portion of each disk spring is fit is formed in either the corresponding pressing plate or the corresponding pressing lid.

16. The piezoelectric motor according to claim 13,
- wherein a convex portion into which an inner circumferential portion of each disk spring is fit is formed in either the corresponding pressing plate or the corresponding pressing lid.

17. A driving device comprising:
the piezoelectric motor according to claim 13.

18. A printing device comprising:
the piezoelectric motor according to claim 13.

19. A robot hand comprising:
the piezoelectric motor according to claim 13.

20. A robot comprising:
the robot hand according to claim 19.

21. An electronic component inspection device which mounts a held electronic component in an inspection socket, and inspects the electrical characteristics of the electronic component,
- wherein the electronic component is aligned with respect to the inspection socket by the piezoelectric motor according to claim 13.

22. An electronic component conveying device which conveys a held electronic component,
- wherein the electronic component is aligned by the piezoelectric motor according to claim 13.

23. An electronic component conveying device comprising:
- a holding device which holds an electronic component;
- a moving device which moves the holding device in directions of three axes in total of a first axis and a second axis perpendicular to each other and a third axis perpendicular to the first axis and the second axis; and
- a control device which controls the operation of the moving device,
- wherein the holding device is embedded with a first piezoelectric motor which moves the electronic component in the direction of the first axis, a second piezoelectric motor which moves the electronic component in the direction of the second axis, and a third piezoelectric motor which rotates the electronic component around the third axis, the first to third piezoelectric motors are the piezoelectric motor according to claim 13.

24. An electronic component inspection device comprising:

- an inspection socket in which an electronic component is mounted, and the electrical characteristics of the electronic component are inspected;
- a holding device which holds the electronic component;
- a moving device which moves the holding device in directions of three axes in total of a first axis and a second axis perpendicular to each other and a third axis perpendicular to the first axis and the second axis;
- an imaging device which is provided on the first axis or the second axis when viewed from the inspection socket to detect a posture of the electronic component mounted in the inspection socket;
- an upstream-side stage which conveys the electronic component from the inspection socket to a predetermined position on the first axis or the second axis connecting the imaging device;
- a downstream-side stage which conveys the electronic component from a predetermined position opposite to the side on which the imaging device is provided when viewed from the inspection socket; and
- a control device which controls the operation of the moving device, wherein the control device includes:

- a first control unit which moves the holding device holding the electronic component conveyed by the upstream-side stage onto the imaging device,
- a second control unit which moves the holding device to mount the electronic component whose posture is confirmed by the imaging device in the inspection socket, and
- a third control unit which moves the holding device to place the electronic component whose electrical characteristics are inspected in the inspection socket from the inspection socket to the downstream-side stage, the holding device is embedded with a first piezoelectric motor which moves the electronic component in the direction of the first axis on the basis of the posture of the electronic component detected by the imaging device, a second piezoelectric motor which moves the electronic component in the direction of the second axis on the basis of the posture of the electronic component detected by the imaging device, and a third piezoelectric motor which rotates the electronic component around the third axis on the basis of the posture of the electronic component detected by the imaging device, and the first to third piezoelectric motors are the piezoelectric motor according to claim 13.

* * * * *